(12) United States Patent
Sato et al.

(10) Patent No.: US 8,723,939 B2
(45) Date of Patent: May 13, 2014

(54) CAPSULE ENDOSCOPE SYSTEM

(75) Inventors: Ryoji Sato, Fuchu (JP); Atsushi Chiba, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/559,765

(22) Filed: Jul. 27, 2012

(65) Prior Publication Data

US 2013/0038711 A1    Feb. 14, 2013

Related U.S. Application Data

(63) Continuation of application No. PCT/JP2012/051200, filed on Jan. 20, 2012.

(30) Foreign Application Priority Data

Jan. 28, 2011   (JP) .................................. 2011-016826

(51) Int. Cl.
| | | |
|---|---|---|
| A61B 1/04 | (2006.01) | |
| A62B 1/04 | (2006.01) | |
| A61B 5/05 | (2006.01) | |
| A61B 1/00 | (2006.01) | |

(52) U.S. Cl.
USPC ............... 348/68; 348/65; 600/424; 600/109; 600/117

(58) Field of Classification Search
None
See application file for complete search history.

(56) References Cited

U.S. PATENT DOCUMENTS

| | | | |
|---|---|---|---|
| 2003/0174205 A1* | 9/2003 | Amling et al. | 348/65 |
| 2007/0073105 A1* | 3/2007 | Honda | 600/118 |
| 2008/0068454 A1* | 3/2008 | Hirakawa | 348/65 |
| 2008/0091065 A1* | 4/2008 | Oshima et al. | 600/109 |
| 2008/0112627 A1 | 5/2008 | Oda | |

(Continued)

FOREIGN PATENT DOCUMENTS

| | | |
|---|---|---|
| EP | 1 920 709 A1 | 5/2008 |
| EP | 2 157 789 A1 | 2/2010 |

(Continued)

*Primary Examiner* — Joseph Ustaris
*Assistant Examiner* — Frederick Bailey
(74) *Attorney, Agent, or Firm* — Scully, Scott, Murphy & Presser, P.C.

(57) ABSTRACT

A capsule endoscope system includes a capsule endoscope which attaches irradiation time of illuminating light required to pick up an image of an object to an item of image data, a magnetic field generating apparatus which generates a guidance magnetic field, an operation section which allows at least one of position and orientation of the capsule endoscope to be changed by manipulating the guidance magnetic field, a control section which attaches posture of a subject, an operating history of the operation section, and an output history of the guidance magnetic field to the item of the image data, a storage unit which stores the item of the image data, and an image play control section which determines, based on at least one piece of the information attached to each item of the image data, whether or not it is necessary to play and display the item of the image data.

1 Claim, 10 Drawing Sheets

(56) References Cited

U.S. PATENT DOCUMENTS

| | | |
|---|---|---|
| 2008/0172255 A1* | 7/2008 | Hirakawa et al. ............... 705/3 |
| 2008/0177177 A1* | 7/2008 | Aoki et al. ..................... 600/424 |
| 2009/0051695 A1 | 2/2009 | Matsuda |
| 2009/0073260 A1* | 3/2009 | Nagase et al. ................. 348/68 |
| 2009/0292174 A1* | 11/2009 | Shigemori ..................... 600/117 |
| 2009/0318762 A1* | 12/2009 | Segawa et al. ................ 600/118 |
| 2010/0030021 A1* | 2/2010 | Minai et al. ................... 600/109 |
| 2010/0067808 A1 | 3/2010 | Matsuzaki |
| 2010/0182412 A1 | 7/2010 | Taniguchi et al. |
| 2010/0194869 A1* | 8/2010 | Matsuzaki ..................... 348/65 |
| 2011/0164126 A1* | 7/2011 | Ambor et al. ................. 348/65 |
| 2012/0113239 A1* | 5/2012 | Krupnik et al. ............... 348/65 |

FOREIGN PATENT DOCUMENTS

| | | |
|---|---|---|
| EP | 2 174 578 A1 | 4/2010 |
| EP | 2 181 642 A1 | 5/2010 |
| JP | 2006-122502 | 5/2006 |
| JP | 2008-119145 | 5/2008 |
| JP | 2009-005020 | 1/2009 |
| JP | 2009-050321 | 3/2009 |
| WO | WO 2008/155974 A1 | 12/2008 |
| WO | WO 2009/008125 A1 | 1/2009 |
| WO | WO 2009/025115 A1 | 2/2009 |

* cited by examiner

FIG.7
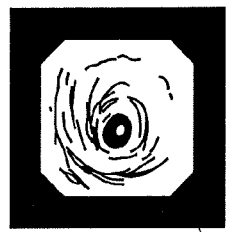
HIGHLIGHTING
FIG.8
PAUSE MARK
FIG.9
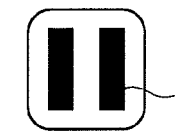 — PAUSE MARK

CAPSULE ENDOSCOPE SYSTEM

CROSS REFERENCE TO RELATED APPLICATION

This application is a continuation application of PCT/JP2012/051200 filed on Jan. 20, 2012 and claims benefit of Japanese Application No. 2011-016826 filed in Japan on Jan. 28, 2011, the entire contents of which are incorporated herein by this reference.

BACKGROUND OF THE INVENTION

1. Field of the Invention

The present invention relates to a capsule endoscope system, and more particularly, to a capsule endoscope system equipped with a capsule endoscope adapted to pick up images of objects in a body cavity of a subject.

2. Description of the Related Art

Conventionally, endoscopes are widely used in a medical field and the like. In the medical field, in particular, endoscopes are used mainly for such applications as observation in living bodies. As one type of the endoscopes described above, a capsule endoscope has recently been put into practical use. The capsule endoscope has capabilities to be placed in a body cavity when swallowed by an examination subject, pick up images of an object in sequence by moving in the body cavity along with peristaltic movements, and transmit the images of the object as an imaging signal to the outside.

Techniques applicable to the capsule endoscope described above include a technique disclosed in Japanese Patent Application Laid-Open Publication No. 2006-122502. The disclosed technique involves determining whether or not a picked-up image of an object is unsuitable for observation and diagnosis and disabling displaying or saving any image determined to be unsuitable.

SUMMARY OF THE INVENTION

A capsule endoscope system according to one aspect of the present invention includes: a capsule endoscope which includes an illumination section adapted to emit illuminating light for illuminating an object in a body cavity of a subject, an imaging section adapted to acquire image data by picking up an image of the object illuminated by the illuminating light, a magnet adapted to generate a magnetic field, and the capsule endoscope being able to attach information about irradiation time of the illuminating light required to pick up the image of the object to each item of the image data acquired by the imaging section and output the image data; a magnetic field generating apparatus adapted to generate a guidance magnetic field to be caused to interact with the magnetic field emitted by the magnet; an operation section adapted to allow at least one of position and orientation of the capsule endoscope to be changed actively by manipulating strength and orientation of the guidance magnetic field; a control section adapted to be able to attach information about posture of the subject in which the image data is acquired by the capsule endoscope, information about an operating history of the operation section recorded when the image data is acquired by the capsule endoscope, and information about an output history of the guidance magnetic field corresponding to the operating history of the operation section to each item of the image data outputted from the capsule endoscope and output the image data; a storage unit adapted to store each item of the image data outputted from the control section; and an image play control section adapted to determine, based on at least one piece of the information attached to each item of the image data stored in the storage unit, whether or not it is necessary to play and display each item of the image data stored in the storage unit and display the image data to be displayed on a display unit.

A capsule endoscope system according to one aspect of the present invention includes: a capsule endoscope which includes an imaging section adapted to acquire image data by picking up an image in a body cavity of a subject and is able to output the image data; a storage unit adapted to acquire at least one piece of examination information about conditions under which the image data is acquired by the capsule endoscope and store the image data by associating the image data with the examination information; and an image play control section adapted to determine, based on at least one piece of the examination information attached to each item of the image data stored in the storage unit, whether or not it is necessary to play and display each item of the image data stored in the storage unit and display the image data to be displayed on a display unit.

BRIEF DESCRIPTION OF THE DRAWINGS

FIG. 7 is a diagram showing an example of a display form used during a pause period;

FIG. 8 is a diagram showing an example of a display form used during a pause period, different from FIG. 7;

FIG. 9 is a diagram showing an example of a display form used during a pause period, different from FIGS. 7 and 8;

DETAILED DESCRIPTION OF THE PREFERRED EMBODIMENTS

Embodiments of the present invention will be described below with reference to the drawings.

(First Embodiment)

FIGS. 1 to 10 concern a first embodiment of the present invention.

Figure 1:
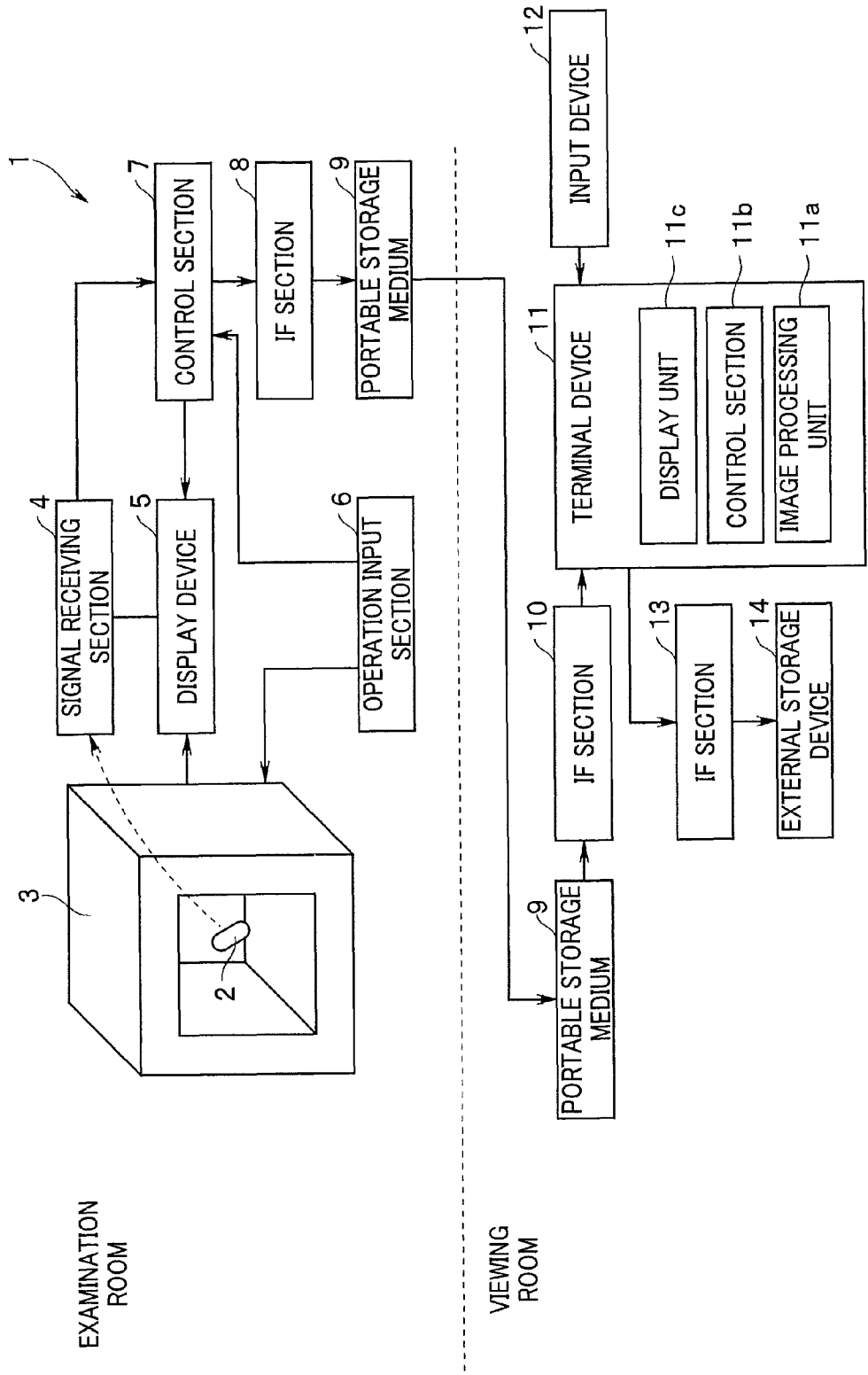
FIG. 1 is a diagram showing an example of principal part of a capsule endoscope system according to an embodiment of the present invention.

FIG. 1 is a diagram showing an example of principal part of a capsule endoscope system according to the present embodiment.

As shown in FIG. 1, the capsule endoscope system 1 includes a capsule endoscope 2, a magnetic field generating apparatus 3, a signal receiving section 4, a display device 5, an operation input section 6, a control section 7, and an interface section (hereinafter abbreviated to an IF section) 8, which are installed in an examination room.

Also, as shown in FIG. 1, the capsule endoscope system 1 includes an IF section 10, a terminal device 11, an input device 12, an IF section 13, and an external storage device 14, which are installed in a viewing room.

Furthermore, the capsule endoscope system 1 includes a portable storage medium 9 (made up of a memory card or the like) configured to be attachable and detachable to/from the IF section 8 and the IF section 10 and adapted to be able to store various information outputted via the IF section 8 in the examination room and output the stored information to the terminal device 11 via the IF section 10 in the viewing room.

The capsule endoscope 2 has a capsule-shaped case and is placed in the digestive tract when swallowed by an examination subject. In the present and subsequent embodiments, description will be given by taking as an example a capsule endoscope of a type which allows guidance and observation in water existing in the digestive tract, i.e., in a body fluid in the digestive tract or in physiological saline or water injected from outside the subject and by assuming that the specific gravity of the capsule endoscope has been set appropriately.

Also, the capsule endoscope 2 includes an imaging section (not shown) adapted to acquire image data by picking up images of an object in a body cavity and an illumination section (not shown) such as an LED adapted to illuminate the object with illuminating light. Both imaging section and illumination section are installed on each end side (i.e., front end side and rear end side) in a long axis direction of the capsule-shaped case. That is, the capsule endoscope 2 can acquire two shots of image data differing from each other in line of sight using the imaging sections installed one each on the opposite end sides in the long axis direction of the capsule-shaped case.

Also, when acquiring image data by picking up images of an object in a body cavity, the capsule endoscope 2 performs light adjustment operation to reduce variations in brightness among the acquired image data. Specifically, the capsule endoscope 2 constantly performs light adjustment operation, for example, in a light-adjusting circuit or the like to make light emission time of the LED shorter than during the previous image data acquisition if brightness of image data acquired the previous time is equal to or higher than a predetermined value, and make light emission time of the LED longer than during the previous image data acquisition if brightness of image data acquired the previous time is lower than a predetermined value.

Furthermore, the capsule endoscope 2 contains a permanent magnet placed in a stationary manner (not shown). Consequently, movement direction, rotation direction, and imaging direction of the capsule endoscope 2 can each be varied via interaction between a guidance magnetic field emitted from the magnetic field generating apparatus 3 according to operation of the operation input section 6 and a magnetic field emitted from the permanent magnet of the capsule endoscope 2.

On the other hand, the capsule endoscope 2 includes an information attaching section (not shown) adapted to attach additional information to a header section of each image data item and a signal transmission section (not shown) adapted to convert the image data with the additional information attached thereto into a wireless signal and output the wireless signal to the outside, where the additional information includes information about the light emission time of the LED (irradiation time of the illuminating light) required to pick up one shot (one frame) of image data.

The magnetic field generating apparatus 3 is placed so as to surround the capsule endoscope 2 placed in the body cavity and is configured to be able to generate a guidance magnetic field according to operation of the operation input section 6.

The signal receiving section 4 includes an antenna and the like capable of receiving the wireless signal outputted from the capsule endoscope 2 and outputs the image data based on the wireless signal to the display device 5 and the control section 7.

The operation input section 6 includes a capsule endoscope operation device (not shown) adapted to allow position and/or orientation (posture) of the capsule endoscope 2 to be changed actively by manipulating strength and orientation of the guidance magnetic field emitted from the magnetic field generating apparatus 3.

Specifically, the capsule endoscope operation device of the operation input section 6 is provided with a reference direction selection switch used, for example, to select one imaging section to serve as a reference for the orientation of the capsule endoscope 2 from the two imaging sections of the capsule endoscope 2.

Also, the capsule endoscope operation device of the operation input section 6 is provided with a magnetic field on/off switch capable of, for example, switching on and off generation of a guidance magnetic field. Also, the capsule endoscope operation device of the operation input section 6 is provided with a guidance mode selector switch capable of changing a guidance mode of the capsule endoscope 2, for example, between a Water Surface mode and a Water Bottom mode, where the Water Surface mode allows observation from a surface of water with the capsule endoscope placed on the surface of the water and the Water Bottom mode allows observation from a bottom of the water.

The Water Surface mode described above is intended to operate the magnetic field generating apparatus 3 in such a way that a vertical magnetic field strong enough to send the capsule endoscope 2 to the water bottom will not be applied to the capsule endoscope 2. Also, the Water Bottom mode described above is intended to operate the magnetic field generating apparatus 3 so as to apply a vertical magnetic field strong enough to submerge at least part of the capsule endoscope 2 in water.

Also, the capsule endoscope operation device of the operation input section 6 is provided with an operation coordinate selector switch capable of changing a coordinate system used for operation of the capsule endoscope 2, for example, between a coordinate system based on the capsule endoscope 2 itself and a coordinate system based on a bed (not shown) placed outside the capsule endoscope 2.

Also, the capsule endoscope operation device of the operation input section 6 is provided with a high-speed movement switch capable of setting movement speed of the capsule endoscope 2 to either high speed or normal speed by changing an upper limit of the strength of the guidance magnetic field generated from the magnetic field generating apparatus 3 according to ON/OFF.

Also, the capsule endoscope operation device of the operation input section 6 is provided with a capture switch which allows any image data such as image data corresponding to a region of interest to be marked by watching images displayed in real time on the display device 5, for example.

Furthermore, the capsule endoscope operation device of the operation input section 6 is provided with a group of switches capable of actively changing position and/or orientation (posture) of the capsule endoscope 2, including an forward/backward switch, an upward/downward switch, a horizontal travel switch, a parallel translation switch capable of dealing with four directions—up, down, left, and right—separately, and an orientation change switch capable of changing orientations in pitch, roll, and yaw directions separately.

The operation input section 6 outputs capsule endoscope operation information to the control section 7, where the capsule endoscope operation information includes an operating history of operations (operation details) performed in various parts of the capsule endoscope operation device and an output history (output status) of magnetic fields emitted from the magnetic field generating apparatus 3 according to the operating history (operation details).

Incidentally, according to the present embodiment, instead of the information about the operating history of the orientation change switch on the capsule endoscope operation device of the operation input section 6, information about detection results produced by directly detecting the orientations of the capsule endoscope 2 in the pitch, roll, and yaw directions may be included in the capsule endoscope operation information.

On the other hand, the operation input section 6 includes input devices such as a keyboard (not shown) which allow operations to be performed with respect to GUIs on various screens displayed on the display device 5.

The control section 7 includes a CPU and the like and performs control needed to display GUIs of a status screen, posture input screen, and the like (described later) on the display device 5 as well as control needed to change a screen displayed on the display device 5 based on the operations performed with respect to GUIs. Furthermore, the control section 7 controls the display device 5 to change display forms of GUIs based on the capsule endoscope operation information outputted from the operation input section 6.

Also, the control section 7 attaches additional information including the capsule endoscope operation information outputted from the operation input section 6 and posture selection information about a selection history of subject's posture on the posture input screen described later to the header section of each image data item outputted from the signal receiving section 4 and outputs to the IF section 8. That is, the additional information has been attached to the header section of the image data outputted from the control section 7 to the IF section 8, where the additional information includes information about the light emission time of the LED in the capsule endoscope 2 required to pick up the image data, the capsule endoscope operation information corresponding to information about the operating history of operations (operation details) performed with respect to the capsule endoscope 2 in picking up the image data, and the posture selection information corresponding to information about the posture assumed by the examination subject in picking up the image data.

Then, the image data with the additional information attached to the headers by the control section 7 is stored in sequence (time-sequentially) in the portable storage medium 9 connected to the IF section 8.

Figure 2:
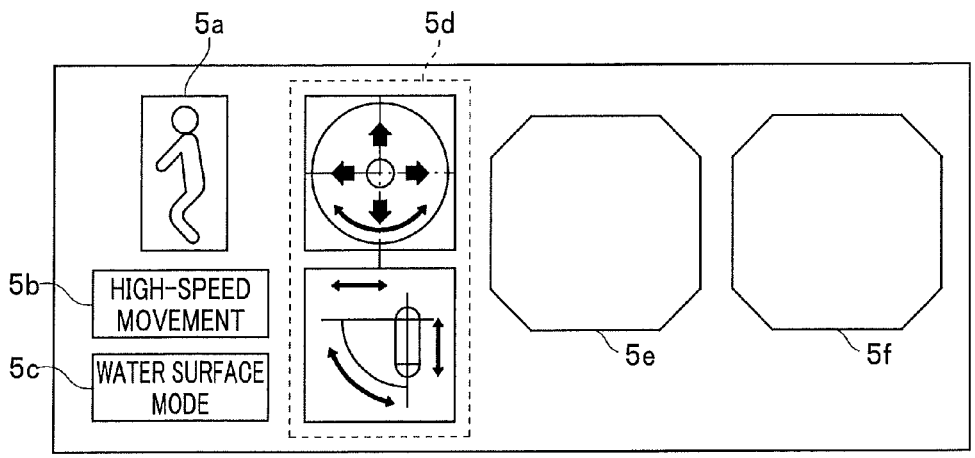
FIG. 2 is a diagram showing an example of a status screen of a capsule endoscope system displayed on a display device in an examination room.

On the other hand, the display device 5 made up of a monitor and the like displays a status screen of the capsule endoscope 2, such as shown in FIG. 2, making it possible to check, in real time, both posture of the capsule endoscope 2 estimated based on operating condition of the magnetic field generating apparatus 3 and information including the image data outputted from the signal receiving section 4.

FIG. 2 is a diagram showing an example of the status screen of the capsule endoscope system displayed on the display device in the examination room.

Specifically, the status screen of the capsule endoscope 2 is displayed on the display device 5, containing posture information 5a which indicates the current posture of the subject; a high-speed movement indicator 5b which indicates whether a High-Speed Movement mode of the capsule endoscope 2 is on or off; guidance mode information 5c which indicates in which mode the capsule endoscope 2 is operated, Water Surface mode, Water Bottom mode, or Magnetic Field Off; posture information 5d which indicates the posture of the capsule endoscope 2 estimated based on the operating condition of the magnetic field generating apparatus 3; image data 5e picked up by one of the imaging sections of the capsule endoscope 2; and image data 5f picked up by the other imaging section of the capsule endoscope 2.

The high-speed movement indicator 5b comes on or goes off in response to on/off state of the high-speed movement switch on the capsule endoscope operation device of the operation input section 6. Specifically, the high-speed movement indicator 5b comes on when the high-speed movement switch on the capsule endoscope operation device of the operation input section 6 is turned on, and goes off when the high-speed movement switch on the capsule endoscope operation device of the operation input section 6 is turned off.

Also, a character string or symbol which represents "Water Surface mode," "Water Bottom mode," or "Magnetic Field Off" is displayed as the guidance mode information 5c according to a selection made on the guidance mode selector switch on the capsule endoscope operation device of the operation input section 6.

Figure 3:
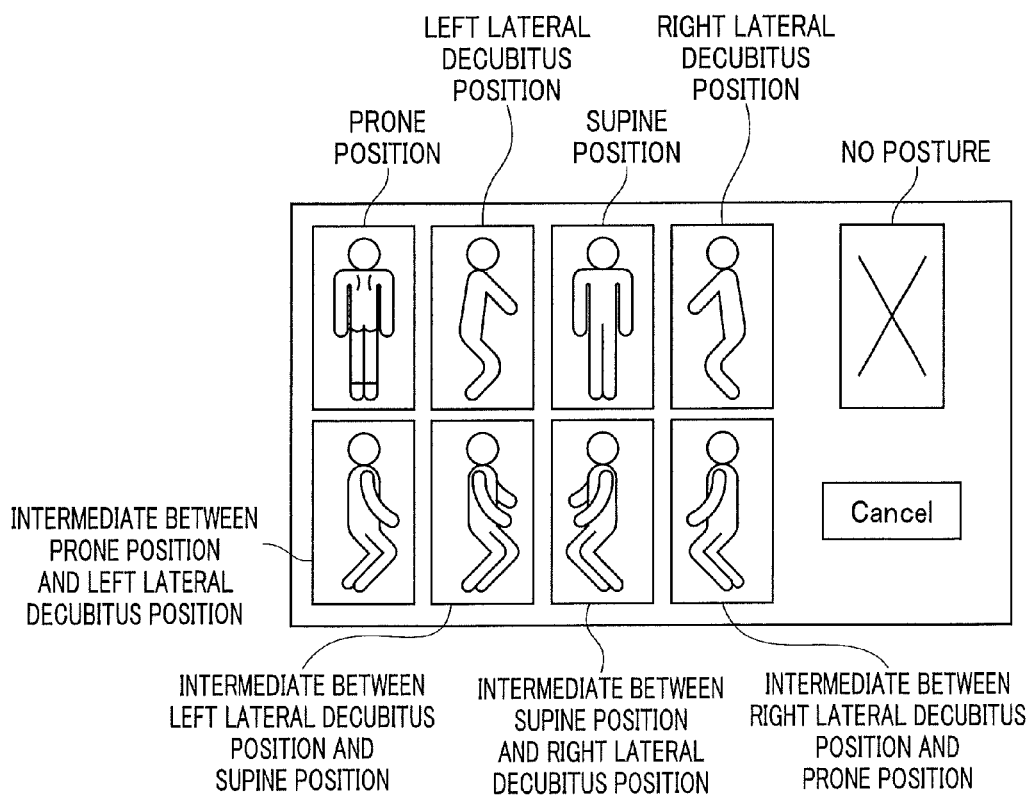
FIG. 3 is a diagram showing an example of a posture input screen displayed on the display device in the examination room.

Now, as an operator in the examination room specifies a display location of the posture information 5a with a cursor by operating the operation input section 6, the screen displayed on the display device 5 changes from the status screen of FIG. 2 to a posture input screen such as illustrated in FIG. 3 as an example.

FIG. 3 is a diagram showing an example of the posture input screen displayed on the display device in the examination room.

Subsequently, by operating the operation input section 6 while visually checking the posture of the subject who has swallowed the capsule endoscope 2, the operator in the examination room selects a posture from among multiple postures being displayed on the posture input screen of FIG. 3. Once the operator selects a desired posture, the screen is transferred from the posture input screen of FIG. 3 to the status screen of FIG. 2.

Incidentally, an "x" button on the posture input screen of FIG. 3 corresponds to "no posture" and can be selected, for example, under a situation in which a guidance magnetic field is not emitted from the magnetic field generating apparatus 3 (when a Magnetic Field Off state is selected via the magnetic field on/off switch). Also, a "Cancel" button on the posture input screen shown in FIG. 3 can be selected, for example, to move to the status screen of FIG. 2 by retaining the previously selected posture. Furthermore, on the posture input screen shown in FIG. 3, postures, such as left lateral decubitus position, supine position, and right lateral decubitus position, selected relatively frequently in actual examinations are displayed together in central part (and neighborhood thereof) of the screen.

Incidentally, for example, when the display device 5 and control section 7 support a touch panel function, the status screen shown in FIG. 2 and the GUI on the posture input screen shown in FIG. 3 are not limited to those operated always via the operation input section 6, and may be a type which is operated when a surface of the display device 5 is touched directly by fingers or the like.

On the other hand, when the portable storage medium 9 is removed from the IF section 8 in the examination room and attached to the IF section 10 in the viewing room, each item of the image data stored in the portable storage medium 9 becomes ready to be outputted to the terminal device 11.

The terminal device 11 includes an image processing unit 11a adapted to apply image processing to the image data outputted from the portable storage medium 9, a control section 11b, and a display unit 11c adapted to display images under the control of the control section 11b.

The control section 11b includes a CPU and the like and classifies (extracts) the image data outputted from the portable storage medium 9, based on at least one piece of information contained in the additional information attached to the header section of each image data item. Based on results of classification (extraction) of the image data outputted from the portable storage medium 9 as well as on switch status of a play mode selector button 121 described later, the control section 11b functioning as a play control section performs various processing related to determination as to whether or not it is necessary to play and display the image data. Details of the processing will be described later.

The control section 11b performs control needed to display GUIs of a play and display screen and the like (described later) on the display unit 11c as well as control needed to change the screen displayed on the display unit 11c based on operation with respect to a GUI. Furthermore, the control section 11b controls the display unit 11c to change display forms of GUIs based on input operation performed via the input device 12.

Also, the control section 11b outputs the image data outputted from the portable storage medium 9 to the IF section 13 by associating the image data with comments (described later) inputted, as required, through operation of the input device 12.

The input device 12 includes a keyboard, plural switches, and the like and accepts input of commands and the like with respect to the terminal device 11.

The external storage device 14 can save the image data and comments associated with each other by the control section 11b, as described later, and includes an HDD (hard disk drive) attachable/detachable with respect to the IF section 13.

Figure 4:
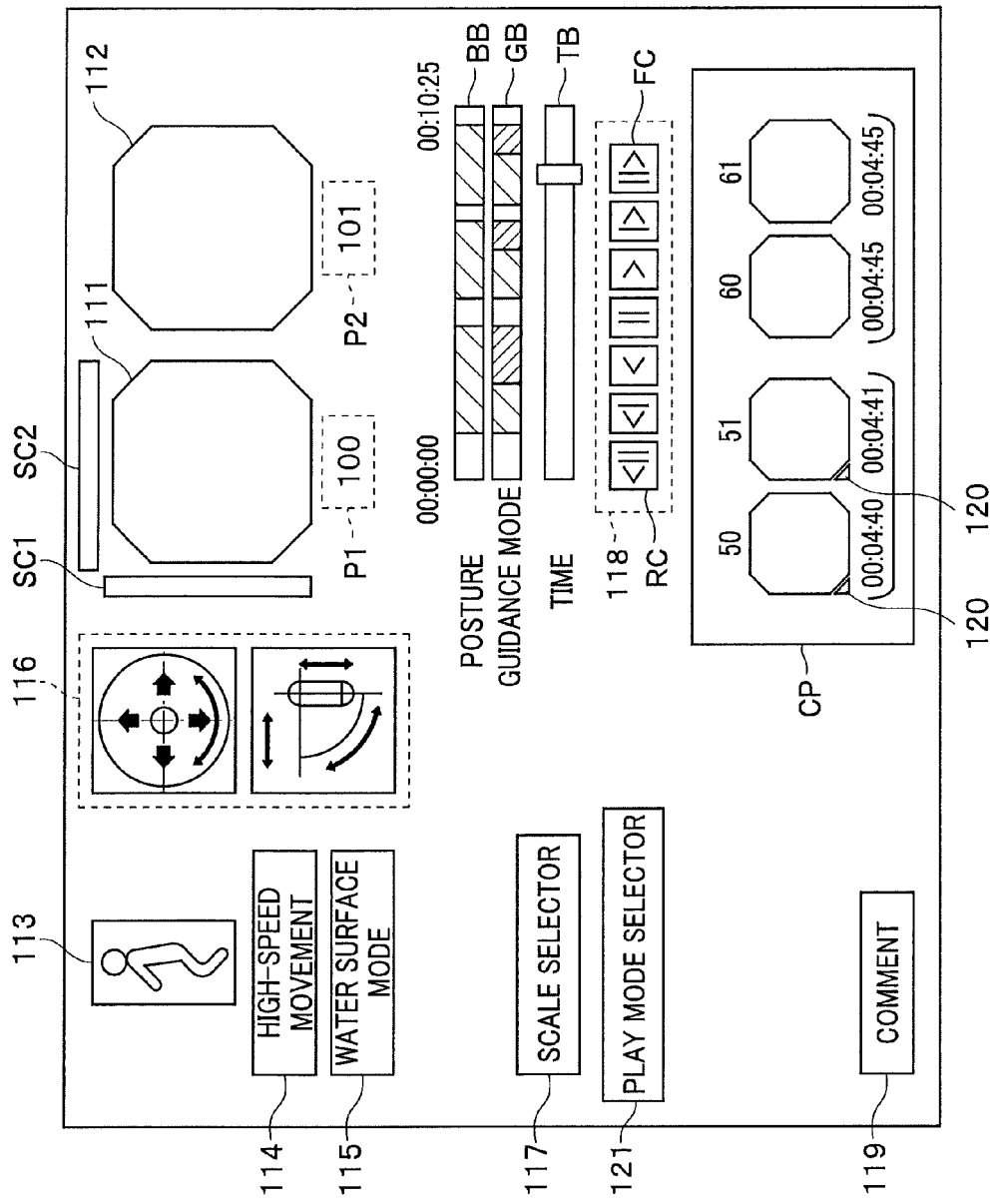
FIG. 4 is a diagram showing an example of a play and display screen displayed on a terminal device in a viewing room.

On the other hand, the display unit 11c of the terminal device 11 is made up of a monitor and the like and adapted to display a play and display screen, such as shown in FIG. 4, making it possible to play and display each item of the image data by referring to related information acquired together with each item of the above-described image data recorded on the portable storage medium 9.

FIG. 4 is a diagram showing an example of the play and display screen displayed on the terminal device in the viewing room.

Specifically, the play and display screen is displayed on the display unit 11c, showing image data 111 picked up by one of the imaging sections of the capsule endoscope 2, image data 112 picked up by the other imaging section of the capsule endoscope 2, posture information 113 which indicates the posture assumed by the subject during acquisition of a set of image data 111 and 112, a high-speed movement indicator 114 which indicates on/off state of the High-Speed Movement mode of the capsule endoscope 2 during acquisition of the set of image data 111 and 112, guidance mode information 115 which indicates the mode used for operation of the capsule endoscope 2 from among Water Surface mode, Water Bottom mode, and Guidance Mode Off during acquisition of the set of image data 111 and 112, and posture information 116 which indicates the posture assumed by the capsule endoscope 2 during acquisition of the set of image data 111 and 112.

Incidentally, the posture information 113, the high-speed movement indicator 114, the guidance mode information 115, and the posture information 116 can be displayed on the display unit 11c when the control section 11b performs control based on results of reading the additional information attached to the header section of each image data item outputted from the portable storage medium 9.

On the other hand, based on the number of shots (number of frames) of the image data outputted from the portable storage medium 9, the control section 11b displays image numbers P1 and P2 on the play and display screen of the display unit 11c, indicating which shots (frames) are the images corresponding to the currently displayed image data 111 and 112 counting from the top.

Also, based on the results of reading the additional information attached to the header section of each image data item outputted from the portable storage medium 9, the control section 11b performs control to display scales in regions SC1 and SC2 located near the image data 111, where the scales are selected through operation of a scale selector switch 117 displayed on the play and display screen.

Specifically, as a first type of scale switchable through operation of the scale selector switch 117, by taking, for example, a direction of gravity as 0°, the control section 11b displays a scale which corresponds to a tilt angle of the capsule endoscope 2 in the region SC1 on the play and display screen of the display unit 11c and displays a scale whereby the parietal side of the subject will be 0° and the toe side of the subject will be 180° in the region SC2 on the play and display screen of the display unit 11c.

Also, as a second type of scale switchable through operation of the scale selector switch 117, by taking, for example, a direction of gravity as 0°, the control section 11b displays a scale which corresponds to a tilt angle of the capsule endoscope 2 in the region SC1 on the play and display screen of the display unit 11c and displays a scale whereby a front direction viewed from location of the operator in the examination room will be 0° and a rear direction of the operator in the examination room will be 180° in the region SC2 on the play and display screen of the display unit 11c.

Incidentally, the above-described first type of scale can be generated based on the results of reading the additional information attached to the header section of each image data item outputted from the portable storage medium 9. Also, the above-described second type of scale can be generated with reference to and through comparison between information about the location of the operator in the examination room inputted in advance and the results of reading the additional information attached to the header section of each image data item outputted from the portable storage medium 9.

Also, based on the results of reading the additional information attached to the header section of each image data item outputted from the portable storage medium 9, the control section 11b displays a guidance mode bar GB which indicates durations of guidance modes used during acquisition of image data on the play and display screen.

The guidance mode bar GB on the play and display screen is displayed in a color coded manner, for example, as shown in FIG. 4 to allow an image interpreter to visually identify a period during which the Water Surface mode is selected, a period during which the Water Bottom mode is selected, and a period during which the guidance mode is off.

On the other hand, based on the results of reading the additional information attached to the header section of each image data item outputted from the portable storage medium 9, the control section 11b displays a posture bar BB which indicates durations of postures taken by the subject during acquisition of image data on the play and display screen.

The posture bar BB on the play and display screen is displayed in a color coded manner, for example, as shown in FIG. 4 to allow the image interpreter to visually identify a period during which no posture is taken, a period during which a first posture (left lateral decubitus position) is taken, a period during which a second posture (supine position) is taken, and a period during which a third posture (right lateral decubitus position) is taken.

Also, the control section 11b displays an image play operation button group 118, which is a GUI that allows operations related to play and display of the set of image data 111 and 112, near the guidance mode bar GB and posture bar BB on the play and display screen. Furthermore, the control section 11b displays a time bar TB near the guidance mode bar GB on the play and display screen, indicating current playback time in relation to total playback time of each image data item outputted from the portable storage medium 9.

The image play operation button group 118 on the play and display screen includes a Forward Cue button FC and a Reverse Cue button RC in addition to a Pause button, a Play button (forward direction and reverse direction), a Fast Forward button, and a Rewind button.

The Forward Cue button FC has a function to advance the playback time to the moment when guidance mode switching occurs (from Water Surface mode to Water Bottom mode, or from Water Bottom mode to Water Surface mode) just after the current playback time.

The Reverse Cue button RC has a function to return the playback time to the moment when guidance mode switching occurs (from Water Surface mode to Water Bottom mode, or from Water Bottom mode to Water Surface mode) just before the current playback time.

On the other hand, based on the results of reading the additional information attached to the header section of each image data item outputted from the portable storage medium 9, the control section 11b displays an image data group marked by operating a Capture button on the operation input section 6, in a set of two in a region CP on the play and display screen of the display unit 11c. Incidentally, it is assumed that an image number and playback time are displayed near each item of image data displayed in the region CP, where the image number indicates which shot (frame) is the image counting from the top and the playback time corresponds to the time at which the image data is acquired.

The control section 11b displays a Comment button 119 on the play and display screen to allow input of comments for each set of image data marked by operating the Capture button on the operation input section 6.

Upon detecting a press of the Comment button 119 through operation of the input device 12, the control section 11b performs control to change the screen displayed on the display unit 11c from the play and display screen of FIG. 4 to a comment input screen (not shown).

Then, the control section 11b saves the comments inputted in the comment input screen and the marked set of image data in the external storage device 14 such as an HDD (hard disk drive) connected to the IF section 13, by associating the comments and the set of image data with each other. Specifically, the control section 11b saves (stores) a text file containing the comments inputted in the comment input screen and two image files corresponding to the marked set of image data in a same folder of the external storage device 14.

Incidentally, it is assumed that when one or more sets of image data for which comments have been inputted in advance by pressing the Comment button 119 are displayed on the play and display screen out of the image data group marked by operating the Capture button on the operation input section 6, a comment mark 120 is attached to each item of image data to allow the image interpreter to visually identify that comments have been inputted.

Also, the control section 11b displays a play mode selector button 121 on the play and display screen to turn on and off a special image play mode which is based on the results of classification of the image data outputted from the portable storage medium 9 unlike normal image play mode which plays images in time sequence.

Now, description will be given of how images are played in the present embodiment when the play mode selector button 121 is on. Incidentally, in the present embodiment, description will be given, assuming that the play mode selector button 121, when pressed, toggles among three states: Off state, Close Examination Mode On state, and Distant View Mode On state. Also, it is assumed that when the play mode selector button 121 is off, the normal image play mode is set. That is, items of the image data outputted from the portable storage medium 9 are played in time sequence.

Based on information about the light emission time of the LED required to pick up one shot (one frame) of image data, i.e., information included in the additional information attached to the header section of each image data item, the control section 11b classifies image data for which the light emission time of the LED is less than a predetermined threshold TH1 (e.g., 5 milliseconds) into a closeup image group (with an imaging region close to a body wall such as the intestinal wall or stomach wall) and classifies image data for which the light emission time of the LED is equal to or more than the predetermined threshold TH1 into a distant-view image group (with an imaging region distant from a body wall such as the intestinal wall or stomach wall).

Then, upon detecting that the play mode selector button 121 has been switched to the Close Examination Mode On state, the control section 11b concatenates only the image data classified into the closeup image group in time sequence and plays the concatenated image data continuously. Also, upon detecting that the play mode selector button 121 has been switched to the Distant View Mode On state, the control section 11b concatenates only the image data classified into the distant-view image group in time sequence and plays the concatenated image data continuously.

Figure 5:
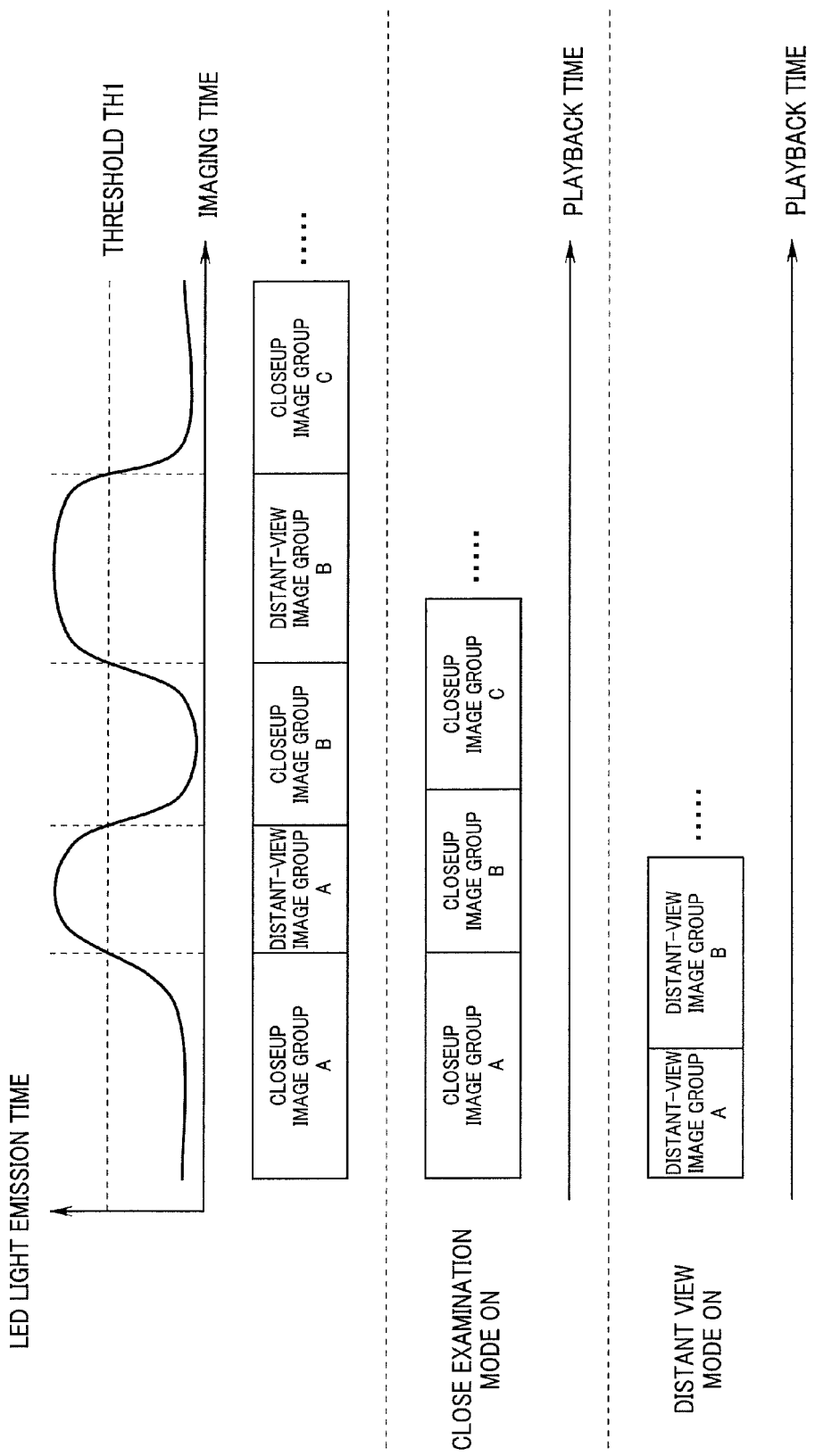
FIG. 5 is a diagram for illustrating an example of image play mode according to a first embodiment.

FIG. 5 is a diagram for illustrating an example of image play mode according to the first embodiment.

Specifically, for example, in a state such as shown in FIG. 5, in which image data classified into plural closeup image groups and image data classified into plural distant-view image groups are intermingled, if the Close Examination mode is turned on, all the image data in a closeup image group A is played, then all the image data in a closeup image group B is played without stopping, and then all the capsule images of closeup image group C are played without stopping. In such a case, the image data classified into the closeup image group A and closeup image group B are not played.

Also, for example, in a state such as shown in FIG. 5, in which image data classified into plural closeup image groups and image data classified into plural distant-view image groups are intermingled, if the Distant View mode is turned on, all the image data in a distant-view image group A is played, and then all the image data in a distant-view image group B is played without stopping. In such a case, the image data classified into the closeup image group A, closeup image group B, and closeup image group C are not played.

Incidentally, when either the Close Examination mode or Distant View mode described above is on, the control section 11b according to the present embodiment may display information about the light emission time of the LED on the play and display screen to allow the image interpreter to recognize an approximate distance from the imaging region to the body wall such as the intestinal wall or stomach wall.

According to the present embodiment described above, since only the image data classified into closeup image groups can be played for observation by turning on, for example, the Close Examination mode, binding hours of the image interpreter can be reduced compared to conventional binding hours. Also, according to the present embodiment described above, since a region of interest can be extracted while playing image data, for example, in the Distant View mode and subsequently only the image data in the extracted region of interest can be played for observation in the Close Examination mode, the binding hours of the image interpreter can be reduced compared to the conventional binding hours.

Incidentally, according to the present embodiment, play of image data may be paused, for example, each time play of an image data item belonging to an image group is finished.

Figure 6:
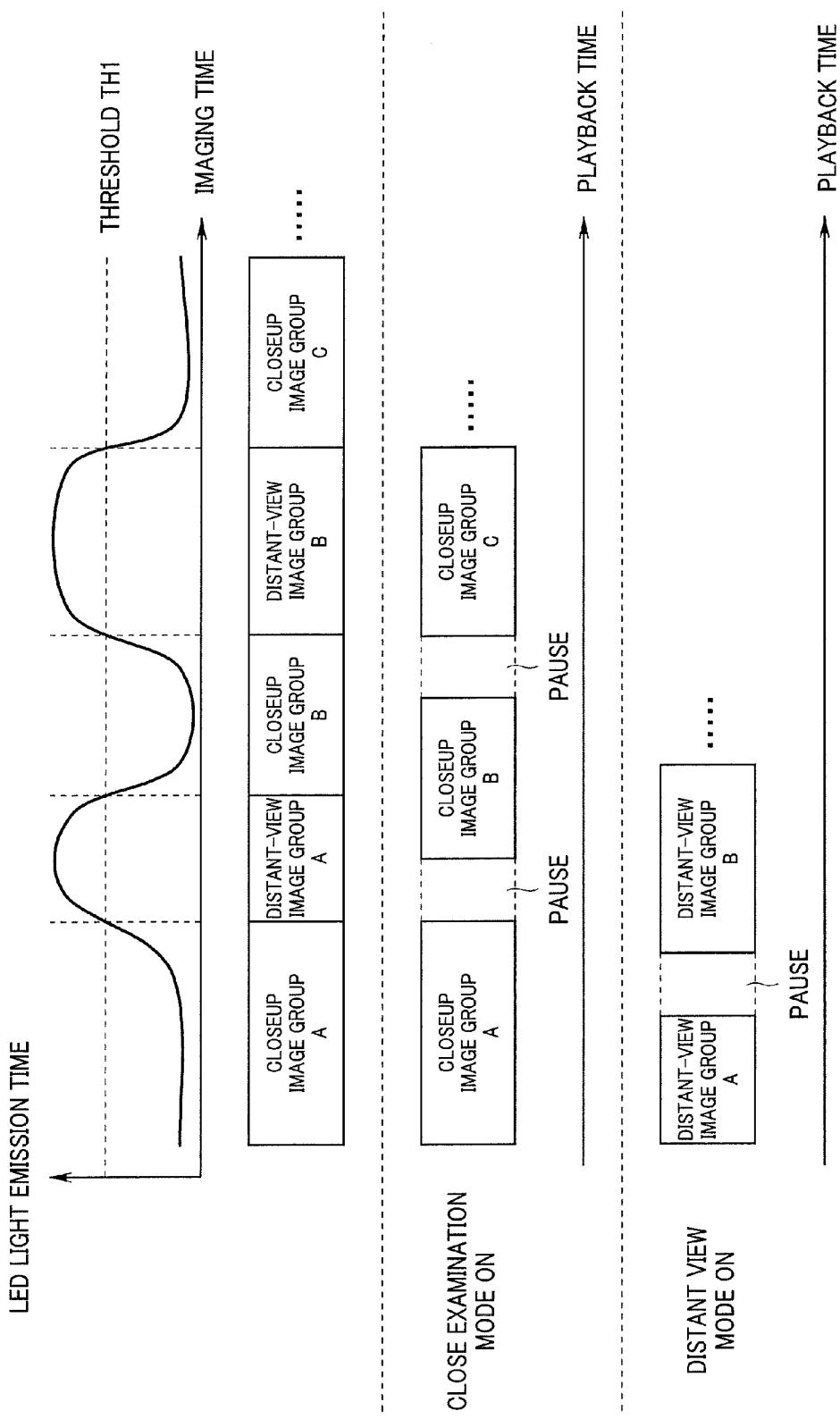
FIG. 6 is a diagram for illustrating a first variation of image play mode according to the first embodiment, different from FIG. 5.

FIG. 6 is a diagram for illustrating a first variation of image play mode according to the first embodiment, different from FIG. 5.

Specifically, for example, in a state such as shown in FIG. 6, in which image data classified into plural closeup image groups and image data classified into plural distant-view image groups are intermingled, if the Close Examination mode is turned on, all the image data in a closeup image group A is played, and just after that, a first pause period is entered. After passage of the first pause period, all the image data in a closeup image group B is played, and just after that, a second pause period is entered. Then, after passage of the second pause period, all the image data in a closeup image group C is played.

Also, for example, in a state such as shown in FIG. 6, in which image data classified into plural closeup image groups and image data classified into plural distant-view image groups are intermingled, if the Distant View mode is turned on, all the image data in a distant-view image group A is played, and just after that, a first pause period is entered. After passage of the first pause period, all the image data in a distant-view image group B is played.

Incidentally, pause period may end after a lapse of a predetermined time or when a predetermined switch or the like on the input device 12 is operated by the image interpreter.

FIG. 7 is a diagram showing an example of a display form used during a pause period.

Also, during the pause period, the last image data displayed up until the start of the pause period may be continued to be displayed or the last image data displayed up until the start of the pause period may be highlighted, for example, as shown in FIG. 7.

FIG. 8 is a diagram showing an example of a display form used during a pause period, different from FIG. 7. FIG. 9 is a diagram showing an example of a display form used during a pause period, different from FIGS. 7 and 8.

Also, for example, as shown in FIGS. 8 and 9, a pause mark which indicates that a pause period is underway may be displayed inside the last image data displayed up until the start of the pause period or externally near the last image data displayed up until the start of the pause period.

According to the above-described first variation of the present embodiment, since the image interpreter can be made to recognize that temporally discontinuous image data is played, the binding hours of the image interpreter can be reduced compared to the conventional binding hours and image data can be played and displayed in such a way that misrecognition is hard to occur at a change of scene.

Also, according to the present embodiment, play speed of image data may be set differently, for example, between the Close Examination mode and Distant View mode.

Specifically, the control section 11b sets the play speed of image data to a speed inversely proportional to the light emission time of the LED if the Close Examination mode is on, and sets the play speed of image data to a speed directly proportional to the light emission time of the LED if the Distant View mode is on.

If the play speed is set in the manner described above, in the Close Examination mode, for example, image data picked up at a location comparatively close to a body wall is played at a relatively low speed and image data picked up at a location comparatively distant from the body wall is played at a relatively high speed.

Also, if the play speed is set in the manner described above, in the Distant View mode, for example, image data picked up at a location comparatively close to a body wall is played at a relatively high speed and image data picked up at a location comparatively distant from the body wall is played at a relatively low speed.

According to the above-described second variation of the present embodiment, in the Close Examination mode, the location of the capsule endoscope 2 in an organ is easy to grasp, and a next candidate region for observation can be checked in advance as well, making it possible to reduce the binding hours of the image interpreter compared to the conventional binding hours.

Also, according to the above-described second variation of the present embodiment, in the Distant View mode, regions considered to be in need of detailed observation can be extracted, and observed quickly as well, making it possible to reduce the binding hours of the image interpreter compared to the conventional binding hours.

On the other hand, according to the present embodiment, for example, in the Close Examination mode in particular, the play order of image data may be rearranged among image groups according to the distance from a body wall.

Figure 10:
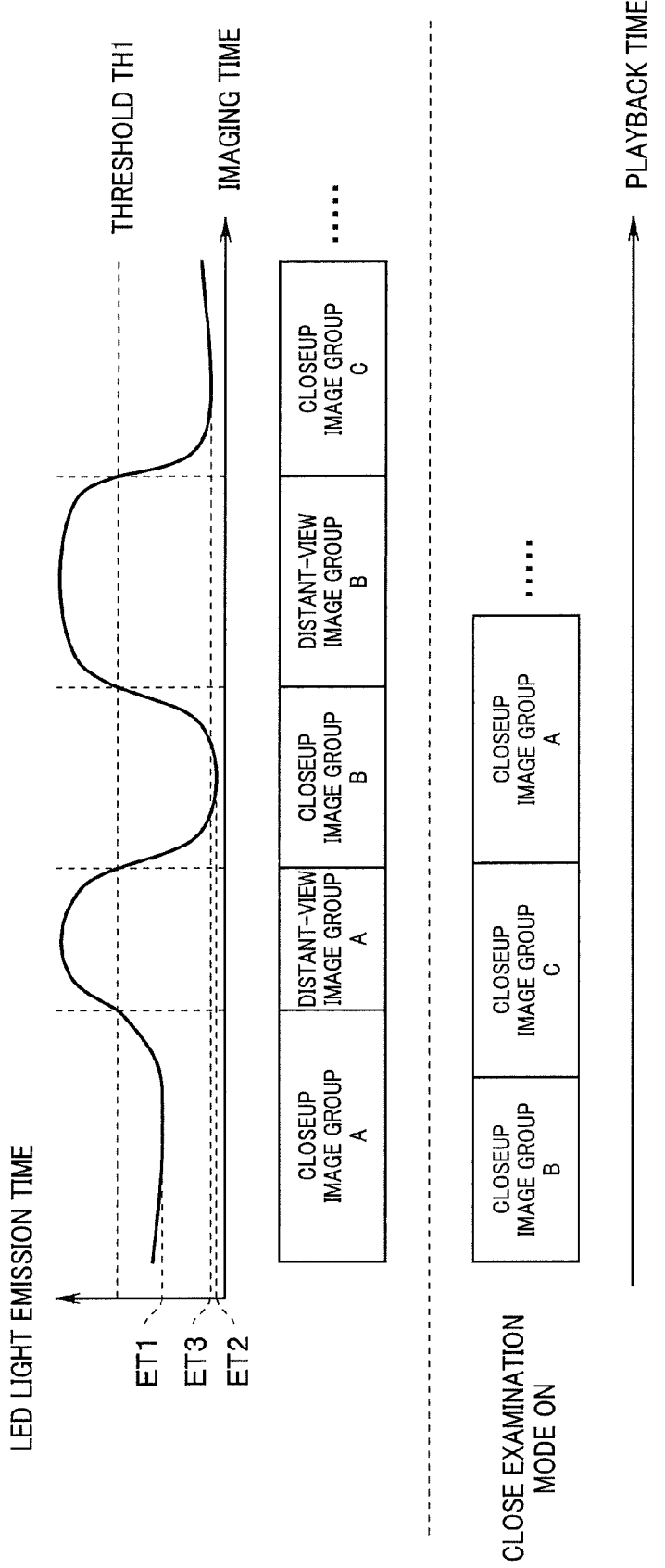
FIG. 10 is a diagram for illustrating a third variation of image play mode according to the first embodiment, different from FIGS. 5 and 6.

FIG. 10 is a diagram for illustrating a third variation of image play mode according to the first embodiment, different from FIGS. 5 and 6.

Specifically, for example, in a state such as shown in FIG. 10, in which image data classified into plural closeup image groups and image data classified into plural distant-view image groups are intermingled, if the Close Examination mode is turned on, based on the additional information on image data in closeup image groups A, B, and C, the control section 11b detects the shortest light emission time ET1 of the LED used in acquiring the image data items in the closeup image group A, the shortest light emission time ET2 of the LED used in acquiring the image data items in the closeup image group B, and the shortest light emission time ET3 of the LED used in acquiring the image data items in the closeup image group C.

Then, in a situation such as illustrated in FIG. 10 as an example, if it is detected that ET2<ET3<ET1 as a result of comparing the shortest light emission time of the LED among the closeup image groups A to C, the control section 11b rearranges the play order such that the image data will be played continuously in the order: the closeup image group B, closeup image group C, and closeup image group A. Through the process of the control section 11b, the play order is rearranged such that the plural closeup image groups will be played in order of increasing LED light emission time, i.e., in order of increasing distance from the body wall.

Incidentally, the control section 11b according to the present embodiment may perform control so as to display a value of the light emission time ET2 during play of the closeup image group B, display a value of the light emission time ET3 during play of the closeup image group C, and display a value of the light emission time ET1 during play of the closeup image group A.

According to the above-described third variation of the present embodiment, in the Close Examination mode, since image data is played in order of increasing distance from the body wall, the binding hours of the image interpreter can be reduced compared to the conventional binding hours and the image data can be played and displayed with a reduced sense of awkwardness at changes of scene.

(Second Embodiment)

Figure 11:
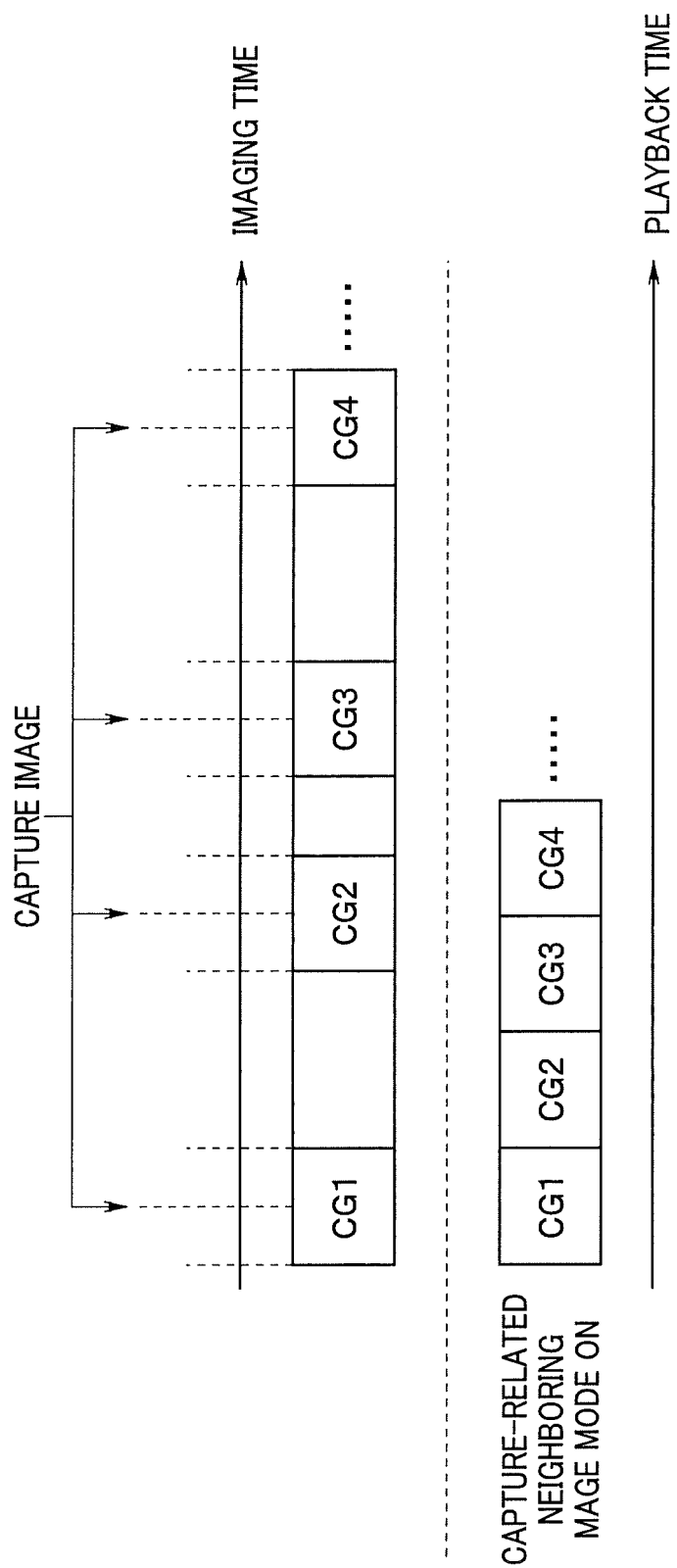
FIG. 11 is a diagram for illustrating an example of image play mode according to a second embodiment.

Next, a second embodiment of the present invention will be described. FIG. 11 concerns the second embodiment of the present invention.

Incidentally, in the present embodiment, detailed description of part similar in configuration to the first embodiment will be omitted. Also, mainly differences from the first embodiment will be described below, including functions of the play mode selector button 121, a method used by the control section 11b to classify (extract) image data, and a method for playing image data based on results of classification (extraction).

Now, description will be given of how images are played in the present embodiment when the play mode selector button 121 is on. Incidentally, in the present embodiment, description will be given, assuming that the play mode selector button 121, when pressed, toggles between two states: Off state and Capture-Related Neighboring Image Mode On state.

Based on a capture switch operating history, which is information included in the additional information in the header section of each image data item outputted from the portable storage medium 9, the control section 11b extracts a capture-related neighboring image group which includes marked capture image data and a predetermined number of shots of image data acquired (e.g., five shots each) before and after the capture image data.

FIG. 11 is a diagram for illustrating an example of image play mode according to the second embodiment.

Specifically, for example, as shown in FIG. 11, if image data items outputted from the portable storage medium 9 includes four shots (four frames) of capture images, capture-related neighboring image groups CG1 to CG4 corresponding to the respective capture images, i.e., to the four shots (four frames), are extracted.

Then, out of the image items outputted from the portable storage medium 9, the control section 11b concatenates only the image data belonging to the capture-related neighboring image groups CG1 to CG4 in time sequence and plays the concatenated image data continuously. That is, when the Capture-Related Neighboring Image mode is turned on, all the image data in the capture-related neighboring image group CG1 is played, then all the image data in the capture-related neighboring image group CG2 is played without stopping, then all the image data in the capture-related neighboring image group CG3 is played without stopping, and then all the image data in the capture-related neighboring image group CG4 is played without stopping.

Incidentally, during play and display of a capture-related neighboring image group, for example, the capture image belonging to the capture-related neighboring image group may be highlighted or the like.

Also, during play and display of a capture-related neighboring image group, a capture image may be newly added, for example, according to marking through operation of the input device 12.

According to the present embodiment described above, since only image data judged by an examiner to fall into a region of interest and image data around the region of interest can be played for observation, the binding hours of the image interpreter can be reduced compared to the conventional binding hours.

Incidentally, in the present embodiment, among the image data belonging to a capture-related neighboring image group, for example, image data to be played and displayed may be narrowed down based on the light emission time of the LED.

Specifically, based on additional information in a header section of capture image data, the control section 11b sets an upper limit value and lower limit value of the light emission time using the light emission time of the LED during acquisition of the capture image data as a base. Then, based on the additional information in the header section of each image data item belonging to the capture-related neighboring image group, the control section 11b makes settings so that the image data for which the light emission time of the LED exceeds the upper limit value and the image data for which the light emission time of the LED falls below the lower limit value will not be played and displayed.

According to the above-described variation of the present embodiment, since it is possible to play and observe only image data judged by the examiner to fall into a region of interest and image data picked up around the region of interest at about the same distance from the body wall as the distance between the region of interest and body wall, the binding hours of the image interpreter can be reduced compared to the conventional binding hours.

(Third Embodiment)

Figure 12:
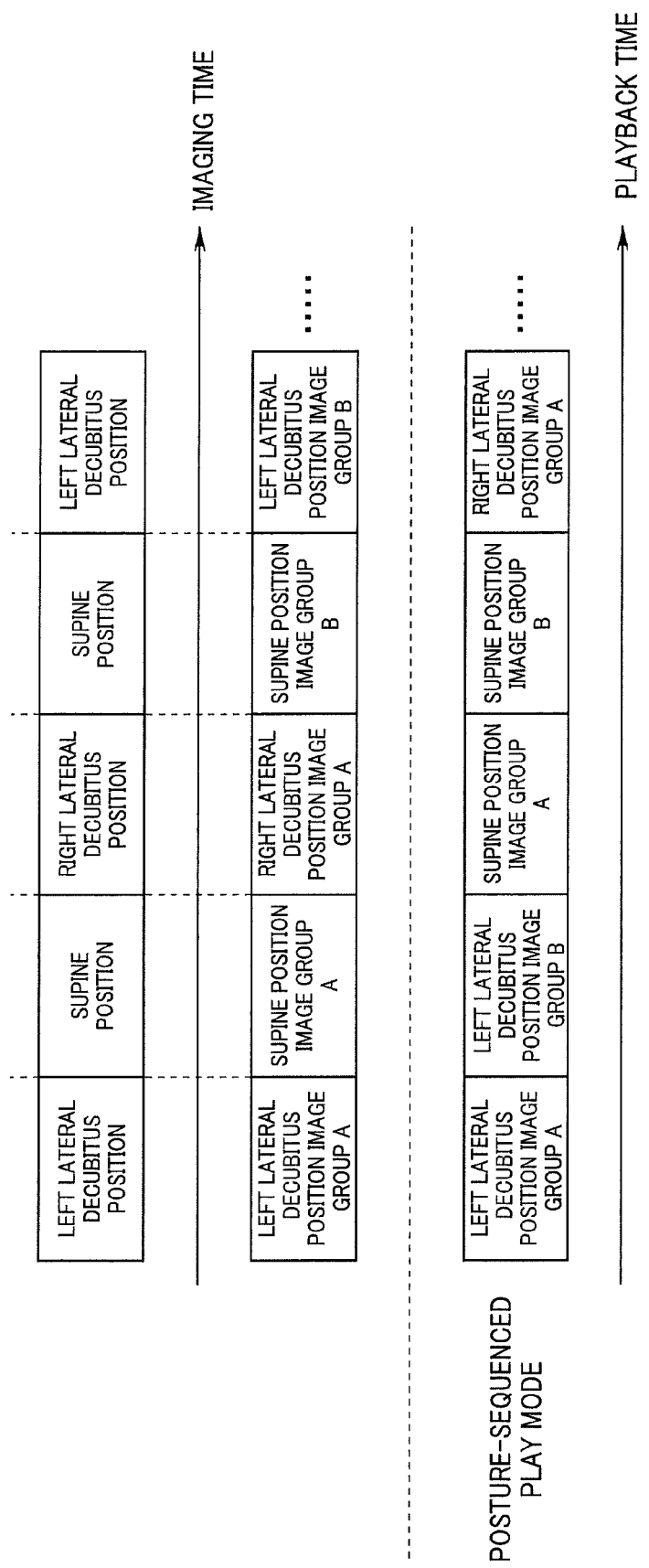
FIG. 12 is a diagram for illustrating an example of image play mode according to a third embodiment.

Next, a third embodiment of the present invention will be described. FIG. 12 concerns the third embodiment of the present invention.

Incidentally, in the present embodiment, detailed description of part similar in configuration to the first and second embodiments will be omitted. Also, mainly differences from the first and second embodiments will be described below, including functions of the play mode selector button 121, a method used by the control section 11b to classify (extract) image data, and a method for playing image data based on results of classification (extraction).

Now, description will be given of how images are played when the play mode selector button 121 is on. Incidentally, in the present embodiment, description will be given, assuming that the play mode selector button 121, when pressed, toggles between two states: Off state and Posture-Sequenced Play Mode On state.

Based on posture selection information, which is information included in the additional information in the header section of each image data item outputted from the portable storage medium 9, the control section 1 lb classifies the image data according to the postures selected on the above-described posture selection screen.

FIG. 12 is a diagram for illustrating an example of image play mode according to the third embodiment.

Specifically, for example, in a state such as shown in FIG. 12, in which image data classified into left lateral decubitus position image groups, image data classified into supine position image groups, and image data classified into a right lateral decubitus position image group are intermingled, if a Posture-Sequenced Play mode is turned on, the control section 11*b* ensures that the image data will be played continuously in the order: a left lateral decubitus position image group A, left lateral decubitus position image group B, supine position image group A, supine position image group B, and right lateral decubitus position image group A.

Regarding the play order of image data in the Posture-Sequenced Play mode, as long as the play order is established based on results of image data classification by posture, the order used may be a fixed order established in advance as a standard play order (e.g., the order: left lateral decubitus position image group, supine position image group, right lateral decubitus position image group, and prone position) or any desired order specified via the input device 12.

According to the present embodiment described above, since image data obtained by presumably picking up images of substantially the same region in a body cavity can be played and displayed continuously, the binding hours of the image interpreter can be reduced compared to the conventional binding hours.

Incidentally, in the present embodiment, items of image data classified as belonging to image groups of the same posture may be further subclassified, for example, based on the posture of the capsule endoscope.

In such a case, after classifying the image data according to the postures selected on the above-described posture selection screen, the control section 11*b* further subclassifies the image data classified by the posture, based on the operating history of the reference direction selection switch and orientation change switch, which is information included in the additional information in the header section of each image data item outputted from the portable storage medium 9.

(Fourth Embodiment)

Next, a fourth embodiment of the present invention will be described.

Incidentally, in the present embodiment, detailed description of part similar in configuration to the first to third embodiments will be omitted. Also, mainly differences from the first to third embodiments will be described below, including functions of the play mode selector button 121, a method used by the control section 11*b* to classify (extract) image data, and a method for playing image data based on results of classification (extraction).

Now, description will be given of how images are played in the present embodiment when the play mode selector button 121 is on. Incidentally, in the present embodiment, description will be given, assuming that the play mode selector button 121, when pressed, toggles between two states: Off state and Blurred-Image Removal Mode On state.

When a Blurred-Image Removal mode is turned on, based on the capsule endoscope operation information included in the additional information in the header section of each image data item outputted from the portable storage medium 9, the control section 11*b* extracts image data for which an amount of change per unit time in the guidance magnetic field emitted from the magnetic field generating apparatus 3 is equal to or larger than a predetermined value, i.e., image data acquired through an operation which changes the position and/or orientation of the capsule endoscope 2 greatly in a short time, as an image group with a large amount of blur.

Then, out of the image data outputted from the portable storage medium 9, by skipping the image data belonging to the image group with a large amount of blur, the control section 11*b* plays and displays the image data not belonging to the image group with a large amount of blur, in time sequence.

Incidentally, when the Blurred-Image Removal mode is on, instead of extracting the image group with a large amount of blur based on the capsule endoscope operation information, the control section 11*b* may extract image data with an amount of blur equal to or larger than a predetermined value as an image group with a large amount of blur based, for example, on calculation results produced by the image processing unit 11*a* by calculating an amount of blur according to spatial frequency of each image data item outputted from the portable storage medium 9.

According to the present embodiment described above, since the image data belonging to the image group with a large amount of blur is not played and displayed, the binding hours of the image interpreter can be reduced compared to the conventional binding hours.

(Fifth Embodiment)

Next, a fifth embodiment of the present invention will be described.

Incidentally, in the present embodiment, detailed description of part similar in configuration to the first to fourth embodiments will be omitted. Also, mainly differences from the first to fourth embodiment will be described below, including functions of the play mode selector button 121, a method used by the control section 11*b* to classify (extract) image data, and a method for playing image data based on results of classification (extraction).

Now, description will be given of how images are played in the present embodiment when the play mode selector button 121 is on. Incidentally, in the present embodiment, description will be given, assuming that the play mode selector button 121, when pressed, toggles among three states: Off state, Magnetic Field Output Image Mode On state, and Magnetic Field Stop Image Mode On state.

When a Magnetic Field Output Image mode or Magnetic Field Stop Image mode is turned on, based on the capsule endoscope operation information included in the additional information in the header section of each image data item outputted from the portable storage medium 9, the control section 11*b* classifies the image data picked up during a period in which the capsule endoscope 2 has been operated actively (a magnetic field is emitted from the magnetic field generating apparatus 3) into an image group of a magnetic field output period and classifies the image data picked up during a period in which the capsule endoscope 2 has not been operated actively (no magnetic field is emitted from the magnetic field generating apparatus 3) into an image group of a magnetic field stop period.

Then, when the Magnetic Field Output Image mode is on, by skipping the image data belonging to the image group of the magnetic field stop period out of the image data outputted from the portable storage medium 9, the control section 11*b* plays and displays the image data belonging to the image group of the magnetic field output period at constant speed in time sequence.

On the other hand, when the Magnetic Field Stop Image mode is on, by skipping the image data belonging to the image group of the magnetic field output period out of the image data outputted from the portable storage medium 9, the control section 11*b* plays and displays the image data belonging to the image group of the magnetic field stop image period at high speed in time sequence.

Incidentally, in the present embodiment, whether or not the capsule endoscope 2 has been operated actively may be determined using an operating history of the magnetic field on/off switch.

Also, in the present embodiment, as the image data belonging to the image group of the magnetic field output period described above, for example, image data belonging to at least one or more image groups acquired when a guidance magnetic field is emitted from the magnetic field generating apparatus 3 in a preset pattern may be played and displayed. Specifically, the control section 11b according to the present embodiment may play and display, in time sequence, for example, one or both sets of image data extractable based on an operating history of the guidance mode selector switch, where the sets of extractable image data are image data belonging to an image group of a period in which the Water Surface mode is selected and image data belonging to an image group of a period in which the Water Bottom mode is selected.

According to the present embodiment described above, when the Magnetic Field Output Image mode is on, since only the image data presumably picked up by the examiner with some intent can be played and displayed, the binding hours of the image interpreter can be reduced compared to the conventional binding hours.

Also, according to the present embodiment described above, when the Magnetic Field Stop Image mode is on, since only the image data presumably picked up without the examiner's intent can be played and displayed, the binding hours of the image interpreter can be reduced compared to the conventional binding hours.

(Sixth Embodiment)

Next, a sixth embodiment of the present invention will be described.

Incidentally, in the present embodiment, detailed description of part similar in configuration to the first to fifth embodiments will be omitted. Also, mainly differences from the first to fifth embodiment will be described below, including functions of the play mode selector button 121, a method used by the control section 11b to classify (extract) image data, and a method for playing image data based on results of classification (extraction).

Now, description will be given of how images are played in the present embodiment when the play mode selector button 121 is on. Incidentally, in the present embodiment, description will be given, assuming that the play mode selector button 121, when pressed, toggles between two states: Off state and Capsule Endoscope Operation Image Mode On state.

When a Capsule Endoscope Operation Image mode is turned on, based on the capsule endoscope operation information included in the additional information in the header section of each image data item outputted from the portable storage medium 9, the control section 11b classifies time-sequentially continuous image data acquired when a same operation is performed continuously with respect to the capsule endoscope 2 (for a predetermined period or longer) into one image group.

Specifically, based on the capsule endoscope operation information, out of the image data outputted from the portable storage medium 9, the control section 11b classifies (extracts) image data acquired when an operation for moving the capsule endoscope 2 forward is performed continuously and image data acquired when an operation for moving the capsule endoscope 2 backward is performed continuously as an image group related to a first operation. That is, the image data belonging to an image group related to the first operation is presumed to be image data acquired during observation which involves zooming up or zooming down.

Also, based on the capsule endoscope operation information, out of the image data outputted from the portable storage medium 9, the control section 11b classifies (extracts) image data acquired when an operation for moving the capsule endoscope 2 vertically upward is performed continuously and image data acquired when an operation for moving the capsule endoscope 2 vertically downward is performed continuously as an image group related to a second operation. That is, the image data belonging to an image group related to the second operation is presumed to be image data acquired during observation which involves scanning in up and down directions.

Also, based on the capsule endoscope operation information, out of the image data outputted from the portable storage medium 9, the control section 11b classifies (extracts) image data acquired when an operation for translating the capsule endoscope 2 in parallel in a left direction is performed continuously and image data acquired when an operation for translating the capsule endoscope 2 in parallel in a right direction is performed continuously as an image group related to a third operation. That is, the image data belonging to an image group related to the third operation is presumed to be image data acquired during observation which involves scanning in left and right directions.

Also, based on the capsule endoscope operation information, out of the image data outputted from the portable storage medium 9, the control section 11b classifies (extracts) image data acquired when an operation for orienting the capsule endoscope 2 in a pitch direction is performed continuously and image data acquired when an operation for orienting the capsule endoscope 2 in a yaw direction is performed continuously as an image group related to a fourth operation. That is, the image data belonging to an image group related to the fourth operation is presumed to be image data acquired when observation is performed with a wide field of view in up and down directions or left and right directions around a region of interest.

Incidentally, based on the capsule endoscope operation information, out of the image data outputted from the portable storage medium 9, the control section 11b may classify (extract) image data acquired when an operation for moving the capsule endoscope 2 forward or backward and an operation for orienting the capsule endoscope 2 in a pitch or yaw direction are performed simultaneously and continuously as an image group related to a fifth operation. That is, the image data belonging to an image group related to the fifth operation is presumed to be image data acquired when fine adjustments are being made during observation which involves zooming up or zooming down to adjust a region of interest displayed on the display device 5 to a size suitable for observation.

Also, based on the capsule endoscope operation information, out of the image data outputted from the portable storage medium 9, the control section 11b may classify (extract) image data acquired when leftward parallel translation and rightward yaw rotation are performed simultaneously and continuously, image data acquired when rightward parallel translation and leftward yaw rotation are performed simultaneously and continuously, image data acquired when vertically upward movement and downward pitch rotation are performed simultaneously and continuously, and image data acquired when vertically downward movement and upward pitch rotation are performed simultaneously and continuously as an image group related to a sixth operation. That is, the image data belonging to an image group related to the sixth operation is presumed to be image data acquired when one region of interest is observed from various angles.

Then, the control section 11b concatenates the image data belonging to the image groups related to the first to sixth operations on an image group basis or image data item basis and plays the concatenated image data continuously.

Also, according to the present embodiment described above, since image data presumably picked up by the examiner with a certain intent can be played continuously, it becomes easy to predict, for example, what kind of image data can be displayed next and possible to relatively easily carry out observations at any desired play speed higher than constant speed. Consequently, the present embodiment described above makes it possible to reduce the binding hours of the image interpreter compared to the conventional binding hours.

(Seventh Embodiment)

Next, a seventh embodiment of the present invention will be described.

Incidentally, in the present embodiment, detailed description of part similar in configuration to the first to sixth embodiments will be omitted. Also, mainly differences from the first to sixth embodiments will be described below, including functions of the play mode selector button 121, a method used by the control section 11b to classify (extract) image data, and a method for playing image data based on results of classification (extraction).

Now, description will be given of how images are played in the present embodiment when the play mode selector button 121 is on. Incidentally, in the present embodiment, description will be given, assuming that the play mode selector button 121, when pressed, toggles between two states: Off state and Capsule Endoscope Guidance Operation Image Mode On state.

When a Capsule Endoscope Guidance Operation Image mode is turned on, based on the capsule endoscope operation information included in the additional information in the header section of each image data item outputted from the portable storage medium 9, the control section 11b classifies (extracts) the image data outputted from the portable storage medium 9.

Specifically, based on the capsule endoscope operation information, out of the image data outputted from the portable storage medium 9, the control section 11b classifies (extracts) image data acquired when the Water Bottom mode is selected as a guidance mode and the imaging section located on the relatively upper side serves as a reference for the orientation of the capsule endoscope 2, as an image group related to a first guidance operation. That is, the image data belonging to an image group related to the first guidance operation is presumed to be image data acquired when observations are being carried out by looking up above the capsule endoscope 2.

Also, based on the capsule endoscope operation information, out of the image data outputted from the portable storage medium 9, the control section 11b classifies (extracts) image data acquired when the Water Bottom mode is selected as a guidance mode and the imaging section located on the relatively lower side serves as a reference for the orientation of the capsule endoscope 2, as an image group related to a second guidance operation. That is, the image data belonging to an image group related to the second guidance operation is presumed to be image data acquired when observations are being carried out by zooming up a body wall located on the bottom of water.

Also, based on the capsule endoscope operation information, out of the image data outputted from the portable storage medium 9, the control section 11b classifies (extracts) image data acquired when the Water Surface mode is selected as a guidance mode and the imaging section located on the relatively upper side serves as a reference for the orientation of the capsule endoscope 2, as an image group related to a third guidance operation. That is, the image data belonging to an image group related to the third guidance operation is presumed to be image data acquired when observations are being carried out by zooming up a body wall located on the upper side.

Also, based on the capsule endoscope operation information, out of the image data outputted from the portable storage medium 9, the control section 11b classifies (extracts) image data acquired when the Water Surface mode is selected as a guidance mode and the imaging section located on the relatively lower side serves as a reference for the orientation of the capsule endoscope 2, as an image group related to a fourth guidance operation. That is, the image data belonging to an image group related to the fourth guidance operation is presumed to be image data acquired when observations are being carried out by looking down below the capsule endoscope 2.

Then, the control section 11b concatenates the image data belonging to the image groups related to the first to fourth guidance operations on an image group basis or image data item basis and plays the concatenated image data continuously.

Incidentally, in the present embodiment, the classification into the image groups related to the first to fourth guidance operations described above may be further performed based on what coordinate system has been selected for use in the operation of the capsule endoscope 2 (which coordinate system has been selected, a coordinate system based on the capsule endoscope 2 itself or a coordinate system based on a bed (not shown) placed outside the capsule endoscope 2).

According to the present embodiment described above, since image data presumably picked up by the examiner with a certain intent can be played continuously, it becomes easy to predict, for example, what kind of image data can be displayed next and possible to relatively easily carry out observations at any desired play speed higher than constant speed. Consequently, the present embodiment described above makes it possible to reduce the binding hours of the image interpreter compared to the conventional binding hours.

It should be noted that the present invention is not limited to the embodiments described above, and needless to say that various alterations and applications are possible without departing from the spirit of the invention. Specifically, the control section 11b may classify the image data outputted from the portable storage medium 9 based, for example, on information included in the additional information in the header section of each image data item outputted from the portable storage medium 9 including information about the light emission time of the LED required to pick up one shot (one frame) of image data, capsule endoscope operation information used in picking up the image data, and posture selection information used in picking up the image data.

(Eighth Embodiment)

Next, an eighth embodiment of the present invention will be described.

Figure 13:
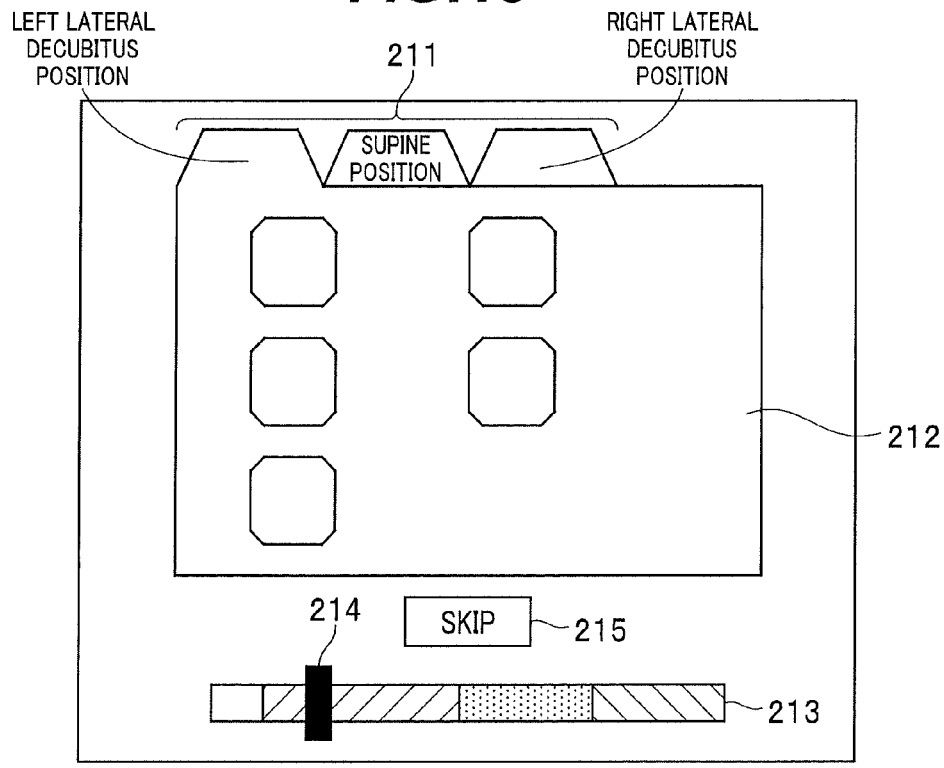
FIG. 13 is a diagram showing an example of a display form of a capture list screen according to an eighth embodiment.
Figure 14:
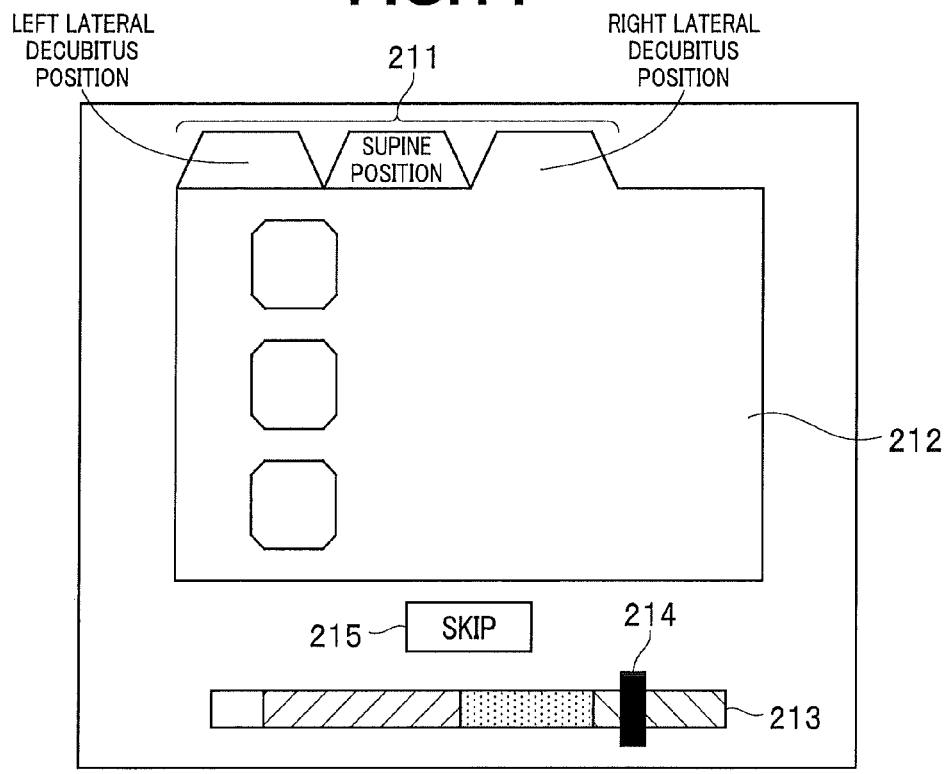
FIG. 14 is a diagram showing an example of a display form of a capture list screen according to the eighth embodiment, different from FIG. 13.

Incidentally, in the present embodiment, detailed description of part similar in configuration to the first to seventh embodiments will be omitted. Also, mainly processes and the like related to part different from those of the first to seventh embodiments will be described in the present embodiment. FIGS. 13 and 14 concern the eighth embodiment of the present invention. Furthermore, the present embodiment will be described by taking as an example a case in which image data is acquired using only one of the two imaging sections provided in the capsule endoscope 2 and processes and the like are performed with respect to image data known in advance to have been acquired by picking up images inside the stomach.

First, based on the results of reading the additional information attached to the header section of each image data item outputted from the portable storage medium 9, the control section 11b extracts a capture image data group made up of one or more items of image data (also referred to as capture image data) marked by operating the Capture button on the operation input section 6.

Based on the posture selection information and capsule endoscope operation information included in the additional information attached to the header section of each image data item outputted from the portable storage medium 9 as well as on preset conditions, the control section 11b performs the process of classifying lines of sight of the capsule endoscope 2 along which individual items of the capture image data included in the capture image data group are acquired.

Specifically, the preset conditions described above may be, for example, that the capsule endoscope 2 is floating in the stomach and that a longitudinal direction of the capsule endoscope 2 is always placed along the direction of gravity when a guidance magnetic field is not emitted from the magnetic field generating apparatus 3. Results of classification produced by the above-described process of the control section 11b by classifying the lines of sight of the capsule endoscope 2 may include, for example, parietal side, toe side, abdominal side, back side, left hand side, and right hand side.

Also, when images are picked up in the stomach, observed regions can be classified into gastric fundal side, gastric corpus side, and vestibular side based on the posture selection information and capsule endoscope operation information. For example, if it is detected based on the posture selection information that left lateral decubitus position is selected with the capsule endoscope 2 floating in water and it is detected based on the capsule endoscope operation information that the line of sight of the capsule endoscope 2 is on the back side, the control section 11b classifies the region observed through the capsule endoscope 2 as the gastric corpus side. Through a similar process, for example, if it is detected that the line of sight of the capsule endoscope 2 is on the parietal side with the capsule endoscope 2 sunken on the bottom, the region observed through the capsule endoscope 2 can be classified as the gastric corpus side.

Incidentally, in the present embodiment, the position and/or orientation of the capsule endoscope 2 may be displaced using, for example, a magnetic guidance apparatus adapted to generate a magnetic field which is caused to interact with the built-in permanent magnet of the capsule endoscope 2 from other permanent magnets.

Specifically, the position and/or orientation of the capsule endoscope 2 may be displaced using a magnetic guidance apparatus which includes a magnetic field generating section equipped with one or more permanent magnets housed in a case, a magnetic-field-state changing drive section adapted to change a state of a magnetic field emitted from the magnetic field generating section, and a translation and rotation mechanism adapted to translate and rotate the magnetic field generating section, wherein the translation and rotation mechanism in turn includes a plan position changing section, a vertical position changing section, an elevation angle changing section, and an angle-of-traverse changing section.

Now, operation and the like of various parts of such a magnetic guidance apparatus will be described.

The plan position changing section, vertical position changing section, elevation angle changing section, and angle-of-traverse changing section translate or rotate the magnetic field generating section while maintaining relative positional relationship among the permanent magnets placed in the magnetic field generating section. Operation of the above parts changes a magnetic field distribution in an effective magnetic field region of the permanent magnets placed in the magnetic field generating section, causing displacement in the position, a tilt angle, and an azimuth angle of the capsule endoscope 2 existing in the effective magnetic field region.

Incidentally, when the position and/or orientation of the capsule endoscope 2 are displaced by the operation of the various parts described above, a state in which magnetization direction of the permanent magnets placed in the magnetic field generating section is oriented in a vertical direction is taken as an initial state. In other words, in such an initial state, a top surface of the magnetic field generating section is parallel to a horizontal plane whose normal direction is set to coincide with the vertical direction (hereinafter simply referred to as a horizontal plane).

The plan position changing section and vertical position changing section are equipped with a translation drive mechanism which includes, for example, a lifter or slider. The plan position changing section with this configuration can translate the magnetic field generating section in the horizontal plane. Also, the vertical position changing section with this configuration can translate the magnetic field generating section in the vertical direction.

The elevation angle changing section rotates the magnetic field generating section around a horizontal axis, and thereby changes an elevation angle $\theta$ between the top surface of the magnetic field generating section and the horizontal plane. Also, the angle-of-traverse changing section rotates the magnetic field generating section around a vertical axis passing through a center of the magnetic field generating section, and thereby changes a traverse angle $\psi$ which corresponds to an angle of traverse of the magnetic field generating section when the above-described initial state is taken as 0°. The elevation angle changing section and angle-of-traverse changing section with these configurations can change the tilt angle and azimuth angle of the capsule endoscope 2 constrained by the magnetic field emitted from the magnetic field generating section, for example, as the angle-of-traverse changing section traverses the magnetic field generating section by the traverse angle $\psi$ and then the elevation angle changing section changes the elevation angle $\theta$.

Incidentally, the magnetic field generating apparatus described in the present embodiment may be used as the magnetic field generating apparatus described in the first to seventh embodiments.

Incidentally, according to the present embodiment, in the process of classifying the lines of sight of the capsule endoscope 2 along which the capture image data is acquired, for example, information obtained by directly detecting the position and orientation (posture) of the capsule endoscope 2 placed in the body cavity of the examination subject may be used instead of the capsule endoscope operation information. Specifically, the position and orientation (posture) of the capsule endoscope 2 can be directly detected if the magnetic field emitted from the permanent magnets of the capsule endoscope 2 is detected and known arithmetic operations are performed based on detection results of the magnetic field.

Also, in the present embodiment, the control section 7 may perform arithmetic operations based, for example, on signal strength of a wireless signal received by the signal receiving section 4 to estimate the position of the capsule endoscope 2 in the subject. Furthermore, position in the subject corresponding to, for example, image data 5e (or 5f) under observation may be displayed on the display device 5 based on results of the arithmetic operations performed by the control section 7.

Also, the position and/or posture of the capsule endoscope 2 estimated based on the guidance magnetic field emitted from the magnetic field generating apparatus 3 may be displayed on the display device 5.

Also, in the present embodiment, the control section 7 may perform arithmetic operations to detect the position of the capsule endoscope 2 based on results of detecting acceleration of the capsule endoscope 2 in the subject.

Specifically, for example, when a configuration is adopted in which an acceleration sensor capable of three-dimensionally detecting the acceleration of the capsule-shaped endoscope 2 is installed in the capsule-shaped endoscope 2 and detection results produced by the acceleration sensor is transmitted as required by being superimposed on the wireless signal, the control section 7 may perform arithmetic operations which involve integrating the acceleration applied to the capsule-shaped endoscope 2, based on the detection results contained in the wireless signal received by the signal receiving section 4, calculating a relative amount of change in the position of the capsule-shaped endoscope 2 corresponding to the integrated acceleration, and calculating the current position of the capsule-shaped endoscope 2 based on the calculated amount of change.

On the other hand, in the present embodiment, in relation to a technique for detecting the position of the capsule-shaped endoscope 2 in the subject using an AC magnetic field, for example, a configuration may be adopted in which an AC magnetic field generating section adapted to generate an AC magnetic field is installed in the capsule-shaped endoscope 2 and plural magnetic field sensors capable of detecting the AC magnetic field is installed in the magnetic field generating apparatus 3.

If such a configuration is adopted, based on detection results produced by the magnetic field sensors by detecting the AC magnetic field emitted from the AC magnetic field generating section of the capsule-shaped endoscope 2, the position and/or orientation of the capsule-shaped endoscope 2 can be calculated continuously. Incidentally, based on the position and/or orientation of the capsule-shaped endoscope 2 calculated in this way, the magnetic field generating apparatus 3 may control generating conditions of a guidance magnetic field.

Also, in the present embodiment, in relation to a technique for detecting the position of the capsule-shaped endoscope 2 in the subject using an AC magnetic field, for example, a configuration may be adopted in which an LC circuit adjusted so as to resonate with a first AC magnetic field is installed in the capsule-shaped endoscope 2 and an AC magnetic field generating apparatus adapted to generate the first AC magnetic field and plural magnetic field sensors are installed in the magnetic field generating apparatus 3.

If such a configuration is adopted, first without the capsule-shaped endoscope 2 being placed in a measurement region (region affected by action of the guidance magnetic field emitted from the magnetic field generating apparatus 3) in the subject, detection results are acquired in advance by detecting the first AC magnetic field emitted from the AC magnetic field generating apparatus of the magnetic field generating apparatus 3 using the plural magnetic field sensors.

Subsequently, with the capsule-shaped endoscope 2 being placed in the measurement region in the subject, when the first AC magnetic field is emitted from the AC magnetic field generating apparatus of the magnetic field generating apparatus 3, the plural magnetic field sensors of the magnetic field generating apparatus 3 detect a second AC magnetic field including a resonant magnetic field emitted from the LC circuit of the capsule-shaped endoscope 2.

Then, strength of the resonant magnetic field emitted from the LC circuit of the capsule-shaped endoscope 2 is calculated based on differences between detection results of the first AC magnetic field and detection results of the second AC magnetic field, and the position and/or orientation of the capsule-shaped endoscope 2 can be calculated continuously based on the calculated strength of the resonant magnetic field.

Also, by acquiring the lines of sight of the capsule endoscope 2 from the capsule endoscope operation information, the control section 11b may classify image data based on the acquired lines of sight and the posture selection information. Specifically, for example, if it is detected based on the posture selection information that left lateral decubitus position is selected with the capsule endoscope 2 floating in water and it is detected based on the capsule endoscope operation information that the line of sight of the capsule endoscope 2 is on the back side, the control section 11b classifies the region observed through the capsule endoscope 2 as image data on the gastric corpus side. Also, for example, if it is detected that left lateral decubitus position is selected in the posture selection information and the line of sight of the capsule endoscope 2 is on the left hand side, the control section 11b classifies the image data to which the posture selection information is attached as image data on the gastric corpus side. Through a similar process, for example, if it is detected that the line of sight of the capsule endoscope 2 is on the craniad side with the capsule endoscope 2 sunken on the bottom, the region observed through the capsule endoscope 2 can be classified as image data on the gastric vestibular side.

Then, based on the additional information attached to each image data item outputted from the portable storage medium 9 and classification results of acquisition regions of capture image data, the control section 11b performs a process for displaying a GUI related to a capture list screen on the display unit 11c, for example, as shown in FIGS. 13 and 14, a process for changing the screen displayed on the display unit 11c based on an operation with respect to the GUI related to the capture list screen, and the like. (Acquisition regions of capture image data are classified for individual items of the capture image data included in the capture image data group.)

Now, the capture list screen shown in FIGS. 13 and 14 will be described. FIG. 13 is a diagram showing an example of a display form of the capture list screen according to the eighth embodiment. FIG. 14 is a diagram showing an example of a display form of the capture list screen according to the eighth embodiment, different from FIG. 13.

The capture list screen displayed on the display unit 11c according to the present embodiment contains a tab group 211, a capture image display area 212, a time bar 213, a time pointer 214, and a skip button 215.

The tab group 211 includes plural tabs containing character strings and the like capable of identifying the postures of the subject individually and provides a capability to select one of the plural tabs.

The capture image display area 212 is an area configured to list items of capture image data which simultaneously satisfy an acquisition region of capture image data and a posture corresponding to a tab selected from the tabs included in the tab group 211, out of capture image data contained in the capture image data group, where the acquisition region is information inputted in advance on a condition input screen (not shown).

The time bar 213 is color-coded by posture, indicating durations of postures taken by the subject during acquisition of image data.

The time pointer 214 is configured to be able to point to any position on the time bar 213.

The skip button 215 provides a capability to give a command to change image data to serve as a starting point for play (play and display) of moving images when the play mode selector button 121 on the play and display screen of FIG. 4 is turned off (when image data outputted from the portable storage medium 9 is played in time sequence), in a predetermined pattern according to the posture of the examination subject.

Next, processes and the like related to various operations performed with respect to the GUI on the capture list screen shown in FIGS. 13 and 14 will be described.

As a result of input operation performed via the input device 12, if it is detected, for example, that "gastric fundal portion" is inputted on the condition input screen (not shown) and that a "left lateral decubitus position" tab is selected from the tab group 211, the control section 11b lists capture image data in the capture image display area 212 according to the detection results and moves the time pointer 214 on the time bar 213 to a position corresponding to a start time of left lateral decubitus position.

Also, as a result of input operation performed via the input device 12, if it is detected, for example, that "gastric fundal portion" is inputted on the condition input screen (not shown) and that a "right lateral decubitus position" tab is selected from the tab group 211, the control section 11b lists capture image data in the capture image display area 212 according to the detection results and moves the time pointer 214 on the time bar 213 to a position corresponding to a start time of right lateral decubitus position.

Furthermore, as a result of input operation performed via the input device 12, if it is detected that one item of capture image data has been selected from the capture image data listed in the capture image display area 212, the control section 11b moves the time pointer 214 to a position corresponding to the selected capture image data item on the time bar 213 and sets the selected capture image data to serve as a starting point for play of moving images when the play mode selector button 121 on the play and display screen of FIG. 4 is turned off.

That is, on the capture list screen shown in FIGS. 13, one of five items of capture image data classified as image data produced by picking up images of a gastric fundal portion in left lateral decubitus position has been set as image data to serve as a starting point for play of moving images when the play mode selector button 121 on the play and display screen of FIG. 4 is turned off. Also, on the capture list screen shown in FIG. 14, one of three items of capture image data classified as image data produced by picking up images of a gastric fundal portion in right lateral decubitus position has been set as image data to serve as a starting point for play of moving images when the play mode selector button 121 on the play and display screen of FIG. 4 is turned off.

On the other hand, as a result of input operation performed via the input device 12, if it is detected that the skip button 215 has been pressed, the control section 11b changes the capture image data to serve as a starting point for play of moving images when the play mode selector button 121 on the play and display screen of FIG. 4 is turned off, in a predetermined pattern according to the posture of the examination subject and moves the position of the time pointer 214 on the time bar 213 so as to point to the position of the capture image data which will serve as a starting point for play of moving images after the change.

Specifically, each time the skip button 215 is pressed, the control section 11b changes the capture image data to serve as a starting point for play of moving images when the play mode selector button 121 on the play and display screen of FIG. 4 is turned off, by toggling, for example, among start time of left lateral decubitus position, start time of supine position, start time of right lateral decubitus position and start time of left lateral decubitus position, and then moves the position of the time pointer 214 on the time bar 213 so as to point to the position of the capture image data which will serve as a starting point for play of moving images after the change.

Alternatively, each time the skip button 215 is pressed, the control section 11b changes the capture image data to serve as a starting point for play of moving images when the play mode selector button 121 on the play and display screen of FIG. 4 is turned off, by toggling, for example, among start time of left lateral decubitus position, end time of left lateral decubitus position, start time of supine position, end time of supine position, start time of right lateral decubitus position, end time of right lateral decubitus position and start time of left lateral decubitus position, and then moves the position of the time pointer 214 on the time bar 213 so as to point to the position of the capture image data which will serve as a starting point for play of moving images after the change.

Incidentally, although an example of classifying the lines of sight of the capsule endoscope 2 and imaging regions in relation to capture image data has been shown in the present embodiment, image play may be carried out based on classification results, and furthermore, image play speed and image play sequence may be changed according to imaging regions as in the case of the first to seventh embodiments.

Incidentally, the control section 11b according to the present embodiment may acquire results of classification of image data in relation to an observation field of view of the capsule endoscope 2 based, for example, on information about an angle of view (visual field range) of the capsule endoscope 2 read from memory or the like (not shown) and on information about the light emission time of the LED required to pick up one shot (one frame) of image data and perform such a process that will display a capture list screen according to the acquired classification results on the display unit 11c.

Also, when listing image data in the capture image display area 212 of the capture list screen, the control section 11b according to the present embodiment may at the same time display, for example, information capable of identifying, on an image data item basis, whether or not a guidance magnetic field is generated from the magnetic field generating apparatus 3.

On the other hand, the control section 11b according to the present embodiment may perform such a process that will display a capture list screen without the tab group 211 on the display unit 11c.

Specifically, out of the image data contained in the capture image data group, the control section 11b according to the present embodiment may list, for example, all the image data items whose classification results coincide with image data acquisition region information inputted in advance on the condition input screen (not shown), in the capture image display area 212. Alternatively, the control section 11b according to the present embodiment may, for example, list all the image data contained in the capture image data group and furthermore in the capture image display area 212, high-light the image data items whose classification results coincide with the image data acquisition region information inputted in advance on the condition input screen (not shown).

Also, in the present embodiment, choices for the starting point for play of moving images when the play mode selector button 121 is turned off are not limited to capture images listed for selection in the capture image display area 212 of the capture list screen, and may be, for example, capture images associated with locus of movement of the capsule endoscope 2 or capture images associated with respective regions contained in an organ model of a human body if provided in a selectable fashion.

(Ninth Embodiment)

Next, a ninth embodiment of the present invention will be described.

Incidentally, in the present embodiment, detailed description of part similar in configuration to the first to eighth embodiments will be omitted. Also, mainly processes and the like related to part different from the first to seventh embodiments will be described in the present embodiment. Furthermore, the present embodiment will be described by taking as an example a case in which image data is acquired using only one of the two imaging sections provided in the capsule endoscope 2 and processes and the like are performed with respect to image data known in advance to have been acquired by picking up images inside the stomach.

The capsule endoscope 2 has a capsule-shaped case and is placed in the digestive tract when swallowed by an examination subject. When specific gravity and center-of-gravity position of the capsule endoscope 2 have been set appropriately, the direction of gravity can be observed in water in the digestive tract, i.e., in a body fluid existing in the digestive tract or in physiological saline or water injected from outside the subject. The capsule endoscope 2 according to the present embodiment allows the direction of gravity to be observed without using magnets. To change the observed region, the subject is instructed to change posture and the observation field of view in the stomach is changed with respect to the direction of gravity, changing the observed region.

Based on the posture selection information and capsule endoscope operation information included in the additional information attached to the header section of each image data item outputted from the portable storage medium 9 as well as on preset conditions (observation of the direction of gravity, and the like), the control section 11b performs the process of classifying the lines of sight of the capsule endoscope 2 along which individual items of the capture image data included in the capture image data group are acquired.

For example, if it is detected that left lateral decubitus position is selected in the posture selection information, it can be determined that the line of sight of the capsule endoscope is on the back side which corresponds to the direction of gravity and the image data can be classified as belonging to the gastric corpus side.

Also, in the process of classifying the lines of sight of the capsule endoscope 2 along which the capture image data is acquired, for example, the position detection apparatus described in the eighth embodiment may be used to obtain information by directly detecting the position and orientation (posture) of the capsule endoscope 2 placed in the body cavity of the examination subject. Specifically, with a configuration in which the capsule endoscope in the subject is provided with a position-detecting magnetic field generating section, if the magnetic field emitted from the capsule endoscope is detected outside the subject and known arithmetic operations are performed based on detection results of the magnetic field, the position and orientation (posture) of the capsule endoscope can be detected directly.

Also, according to the present embodiment, as with the eighth embodiment, the regions observed through the capsule endoscope 2 can be classified based on the posture selection information and on the position and orientation of the capsule endoscope detected by the position detection apparatus.

Also, according to the present embodiment, as with the eighth embodiment, the capture image data can be displayed in a display format such as shown in FIGS. 13 and 14.

Incidentally, although an example of classifying the lines of sight (imaging regions) of the capsule endoscope 2 in relation to capture image data has been shown in the present embodiment, image play may be carried out based on classification results as in the case of the first to seventh embodiments, and furthermore, image play speed and image play sequence may be changed according to imaging regions.

According to the present embodiment described above, since images can be played using a desired capture image as a starting point, the binding hours of the image interpreter can be reduced compared to the conventional binding hours.

It should be noted that the present invention is not limited to the embodiments described above, and needless to say that various alterations and applications are possible without departing from the spirit of the invention.

What is claimed is:

1. A capsule endoscope system comprising:
a capsule endoscope comprising:
an illumination section adapted to emit illuminating light for illuminating an object in a body cavity of a subject,
an imaging section adapted to acquire image data by picking up an image of the object illuminated by the illuminating light, and
a magnet adapted to generate a magnetic field;
a magnetic field generating apparatus configured to generate a guidance magnetic field to be caused to interact with the magnetic field emitted by the magnet;
an operation section configured to allow at least one of position and orientation of the capsule endoscope to be changed actively by manipulating strength and orientation of the guidance magnetic field;
a control section configured to be able to attach posture selection information of that indicates which posture of a plurality of predetermined postures the subject is in when the image data is acquired by the capsule endoscope, operating history information that indicates an operating history of the operation section recorded when the image data is acquired by the capsule endoscope, and output history information that indicates an output history of the guidance magnetic field corresponding to the operating history information to each item of the image data outputted from the capsule endoscope and output the image data;
a storage unit configured to store each item of the image data outputted from the control section;
an image classifying section configured to classify each item of the image data stored in the storage unit as an image data group for each observed region of the capsule endoscope, based on the posture selection information and at least one of the operating history information and the output history information of the information attached to each item of the image data stored in the storage unit; and
an image play control section configured to play and display each item of the image data stored in the storage unit for each image data group classified by the image classifying section, wherein the image classifying section is configured to classify each item of the image data stored in the storage unit into an image data group of a gastric fundal portion, an image data group of a gastric corpus side, and an image data group of a vestibular side.

\* \* \* \* \*